US009178161B2

(12) United States Patent
Kosuge et al.

(10) Patent No.: US 9,178,161 B2
(45) Date of Patent: Nov. 3, 2015

(54) BENZO[C]PHENANTHRENE COMPOUND AND ORGANIC LIGHT-EMITTING DEVICE CONTAINING SAME

(75) Inventors: Tetsuya Kosuge, Yokohama (JP); Jun Kamatani, Tokyo (JP); Hiroyuki Tomono, Namazu (JP)

(73) Assignee: Canon Kabushiki Kaisha, Tokyo (JP)

( * ) Notice: Subject to any disclaimer, the term of this patent is extended or adjusted under 35 U.S.C. 154(b) by 499 days.

(21) Appl. No.: 13/512,866

(22) PCT Filed: Nov. 11, 2010

(86) PCT No.: PCT/JP2010/070521

§ 371 (c)(1), (2), (4) Date: May 30, 2012

(87) PCT Pub. No.: WO2011/068034

PCT Pub. Date: Jun. 9, 2011

(65) Prior Publication Data

US 2012/0235888 A1 Sep. 20, 2012

(30) Foreign Application Priority Data

Dec. 2, 2009 (JP) ................................. 2009-274965

(51) Int. Cl.
*H01L 51/00* (2006.01)
*C07C 13/567* (2006.01)
(Continued)

(52) U.S. Cl.
CPC .......... *H01L 51/0054* (2013.01); *C07C 13/567* (2013.01); *C07C 15/38* (2013.01);
(Continued)

(58) Field of Classification Search
CPC ............................ H01L 51/0054; C07C 15/38
USPC ...................................................... 585/26, 27
See application file for complete search history.

(56) References Cited

U.S. PATENT DOCUMENTS

2010/0096982 A1* 4/2010 Eum et al. ..................... 313/504
2010/0314644 A1* 12/2010 Nishimura et al. ............. 257/98
2011/0288292 A1* 11/2011 Parham et al. .................. 544/35

FOREIGN PATENT DOCUMENTS

CN 102282234 A 12/2011
JP 2009-130142 A 6/2009
(Continued)

OTHER PUBLICATIONS

Sayed,M.A.et al.,Synthesis of some benzo phenanthrene derivatives,Egyptian Journal of Chemistry,1989,vol. 32,No. 5,p. 547-557.
(Continued)

*Primary Examiner* — William Boddie
*Assistant Examiner* — Jeffrey A Parker
(74) *Attorney, Agent, or Firm* — Canon U.S.A. Inc., IP Division

(57) ABSTRACT

There is provided a benzo[c]phenanthrene compound represented by formula [1]:

[Chem. 2]

[1]

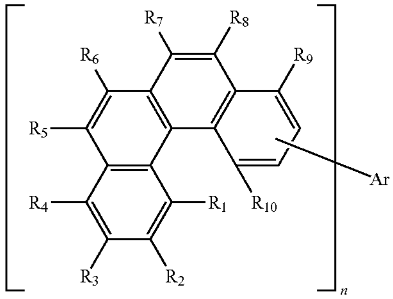

wherein $R_1$ to $R_{10}$ are each independently selected from a hydrogen atom, an alkyl group, an alkoxy group, an aromatic hydrocarbon group, and a heteroaromatic group; n represents an integer of 1 to 3, when n represents 2 or more, $R_1$'s in different benzo[c]phenanthrene rings may be the same or different, and the same is true for $R_2$'s to $R_{10}$'s in different benzo[c]phenanthrene rings; Ar represents an n-valent substituent and represents an aromatic hydrocarbon group or a heteroaromatic group, or Ar may represent a single bond when n represents 2.

13 Claims, 1 Drawing Sheet

(51) Int. Cl.

| | |
|---|---|
| ***C07C 15/38*** | (2006.01) |
| ***C07C 22/08*** | (2006.01) |
| ***C07C 43/21*** | (2006.01) |
| ***C09K 11/06*** | (2006.01) |
| ***H01L 51/50*** | (2006.01) |
| ***H05B 33/14*** | (2006.01) |

(52) U.S. Cl.

CPC ................ *C07C 22/08* (2013.01); *C07C 43/21* (2013.01); *C09K 11/06* (2013.01); *H01L 51/0058* (2013.01); *H01L 51/5048* (2013.01); *H05B 33/14* (2013.01); *C07C 2103/18* (2013.01); *C07C 2103/26* (2013.01); *C07C 2103/42* (2013.01); *C09K 2211/1011* (2013.01); *H01L 51/006* (2013.01); *H01L 51/0055* (2013.01); *H01L 51/0072* (2013.01); *H01L 2251/308* (2013.01)

(56) References Cited

FOREIGN PATENT DOCUMENTS

| | | | |
|---|---|---|---|
| WO | 2010/83869 | A1 | 7/2010 |
| WO | 2010/143434 | A1 | 12/2010 |

OTHER PUBLICATIONS

Laarhoven,W.H.et al.,Chirality and conformational changes in 4-phenyphenanthrenes and 1-phenylbenzo phenanthrene derivatives,Tetrahedron,1978,vol. 34,No. 6,p. 769-777.

* cited by examiner

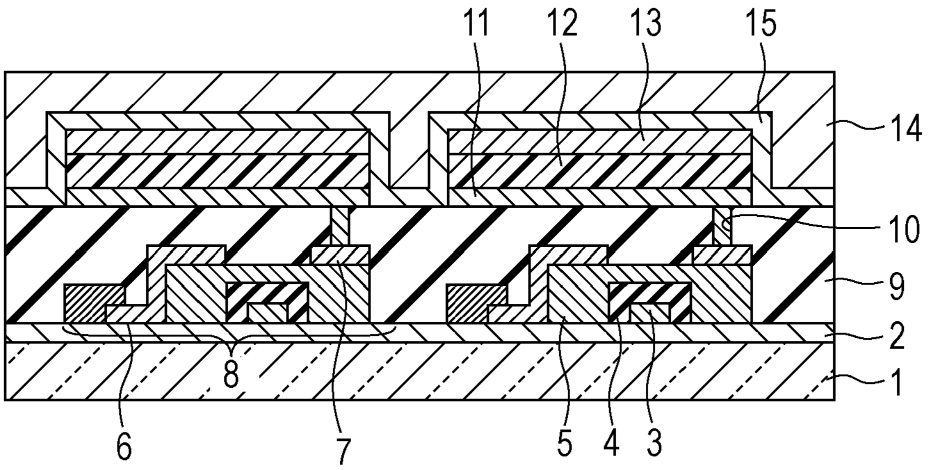
11
12
13
15
14
10
9
2
1
8
6
7
5
4
3

BENZO[C]PHENANTHRENE COMPOUND AND ORGANIC LIGHT-EMITTING DEVICE CONTAINING SAME

TECHNICAL FIELD

The present invention relates to a new benzo[c]phenanthrene compound and an organic light-emitting device containing the compound.

BACKGROUND ART

An organic light-emitting device includes a light-emitting layer provided between an anode and a cathode, which are a pair of electrodes, the light-emitting layer containing a fluorescent organic compound or a phosphorescent organic compound.

There is room for improvement in luminous efficiency and durability.

PTL 1 discloses a benzo[c]phenanthrene derivative serving mainly as a host compound in a phosphorescent layer, the derivative being typified by H03 described below and having an aromatic substituent at the 5-position of a benzo[c]phenanthrene ring.

[Chem. 1]

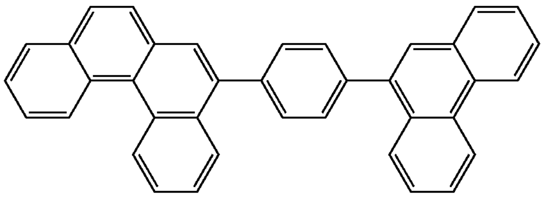

H03

CITATION LIST

Patent Literature

PTL 1 Japanese Patent Laid-Open No. 2009-130142 (family: none)

SUMMARY OF INVENTION

The compound disclosed in PTL 1 has a large dihedral angle between the benzo[c]phenanthrene ring and the aromatic ring of the substituent, thus resulting in low flatness of the entire compound and poor electron transport properties.

Aspects of the present invention provide a new benzo[c] phenanthrene compound having excellent electron transport properties because of a small dihedral angle. Furthermore, aspects of the present invention provide an organic light-emitting device which contains the compound and which thus has excellent luminous efficiency and driving durability.

Accordingly, aspects of the present invention provide a benzo[c]phenanthrene compound represented by formula [1]:

[Chem. 2]

[1]

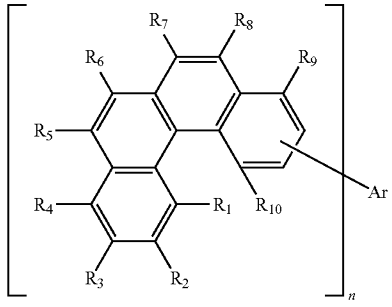

wherein $R_1$ to $R_{10}$ are each independently selected from a hydrogen atom, an alkyl group, an alkoxy group, an aromatic hydrocarbon group, and a heteroaromatic group; n represents an integer of 1 to 3, when n represents 2 or more, $R_1$'s in different benzo[c]phenanthrene rings may be the same or different, and the same is true for $R_2$'s to $R_{10}$'s in different benzo[c]phenanthrene rings; Ar represents an n-valent substituent and an aromatic hydrocarbon group or a heteroaromatic group, or Ar may represent a single bond when n represents 2.

Aspects of the present invention provide the new benzo[c] phenanthrene compound having excellent electron transport properties, and provide the organic light-emitting device which includes the compound and which thus has high luminous efficiency and excellent driving durability.

BRIEF DESCRIPTION OF DRAWINGS

FIG. 1 is a schematic cross-sectional view illustrating organic light-emitting devices and switching elements connected to a corresponding one of the organic light-emitting devices.

DESCRIPTION OF EMBODIMENTS

A benzo[c]phenanthrene compound according to aspects of the present invention is represented by formula [1]:

[Chem. 3]

[1]

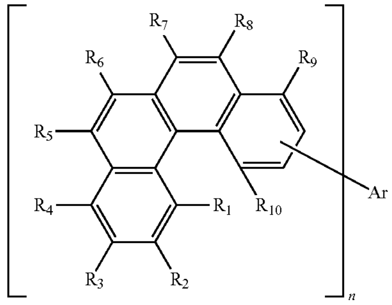

wherein $R_1$ to $R_{10}$ are each independently selected from a hydrogen atom, an alkyl group, an alkoxy group, an aromatic hydrocarbon group, and a heteroaromatic group; n represents an integer of 1 to 3, when n represents 2 or more, $R_1$'s in different benzo[c]phenanthrene rings may be the same or different, and the same is true for $R_2$'s to $R_{10}$'s in different benzo[c]phenanthrene rings; Ar represents an n-valent substituent and an aromatic hydrocarbon group or a heteroaromatic group, or Ar may represent a single bond when n represents 2.

The sentence "Ar may represent a single bond" indicates that benzo[c]phenanthrene molecules are directly bonded to each other. Examples of a compound having this structure include exemplary compounds 301 to 304 described below.

Two bonds of benzo[c]phenanthrene can be linked to Ar and are located at the 2-position and the 3-position of benzo [c]phenanthrene. In the two bonds, one bond that is not linked to Ar is linked to a hydrogen atom.

Specific examples of the alkyl group include methyl, ethyl, propyl, isopropyl, n-butyl, isobutyl, sec-butyl, tert-butyl, n-pentyl, neopentyl, n-hexyl, n-octyl, n-decyl, n-dodecyl, cyclopropyl, cyclobutyl, cyclopentyl, cyclohexyl, norbornyl, and adamantyl groups.

Specific examples of the alkoxy group include methoxy, ethoxy, isopropoxy, tert-butoxy, allyloxy, and benzyloxy groups.

Specific examples of the aromatic hydrocarbon group include phenyl, naphthyl, fluorenyl, phenanthrenyl, anthracenyl, fluoranthenyl, chrysenyl, pyrenyl, tetracenyl, naphthacenyl, triphenylenyl, benzofluoranthenyl, and perylenyl groups.

Specific examples of the heteroaromatic group include pyridyl, pyrazinyl, pyrimidinyl, pyridazinyl, quinolyl, isoquinolyl, azafluorenyl, diazafluorenyl, naphthyridinyl, quinoxalinyl, carbazolyl, phenanthridinyl, phenanthrolinyl, acridinyl, phenazinyl, thienyl, benzothienyl, dibenzothienyl, furyl, benzofuryl, isobenzofuryl, dibenzofuryl, oxazolyl, oxadiazolyl, thiazolyl, and thiadiazolyl.

The alkyl groups, the alkoxy groups, the aromatic hydrocarbon groups, and the heteroaromatic groups may further have substituents. The substituents include alkyl groups, such as methyl, ethyl, and propyl groups; aromatic hydrocarbon groups, such as phenyl, naphthyl, phenanthryl, and fluorenyl groups; heteroaromatic groups, such as thienyl, pyrrolyl, and pyridyl groups; substituted amino groups, such as dimethylamino, diethylamino, dibenzylamino, diphenylamino, ditolylamino, and dianisolylamino groups; alkoxy groups, such as methoxy and ethoxy groups; aryloxy groups, such as phenoxy and naphthoxy groups; halogen atoms, such as fluorine, chlorine, bromine, and iodine atoms; and hydroxy, cyano, and nitro groups.

The fact that benzo[c]phenanthrene compound according to aspects of the present invention is effective in improving the luminous efficiency of an organic light-emitting device will be described below.

To increase the luminous efficiency of an organic light-emitting device, naturally, it is necessary to increase the luminous efficiency a light emission center material contained in a light-emitting layer. In addition, it is necessary to improve the performance of an electron transport layer adjacent to a side of the light-emitting layer adjacent to a cathode. Specifically, improvement in the following four properties leads to high luminous efficiency of the device:

(1) chemical stability;

(2) transporting electrons to the light-emitting layer (electron transport properties);

(3) suppressing the escape of excitons from the light-emitting layer (exciton blocking properties); and (4) suppressing the leak of holes from the light-emitting layer (hole blocking properties).

Typical examples of an electron transport material used for the electron transport layer include organic compounds each having a main skeleton composed of an aromatic hydrocarbon ring, e.g., an anthracene ring or a pyrene ring. The LUMO, which is responsible for electron transport, of such an electron transport material having a main skeleton composed of an aromatic hydrocarbon ring is present in the main skeleton containing only highly stable hydrocarbon. This results in the very high chemical stability of the electron transport material when the electron transport material is used for the electron transport layer.

Fused polycyclic aromatic hydrocarbon rings each having a wide π-conjugated plane that contributes significantly to improve the electron transport properties can be used as such an aromatic hydrocarbon ring. The inventors have focused on a benzo[c]phenanthrene ring, which is one of the fused polycyclic aromatic hydrocarbon rings and have conceived a benzo[c]phenanthrene compound having a main skeleton composed of the ring.

To further improve the electron transport properties of the benzo[c]phenanthrene compound, the π conjugation constituting the LUMO needs to extend throughout the molecule, centering around the benzo[c]phenanthrene ring. To that end, it is necessary to reduce torsion around the bond axis of the benzo[c]phenanthrene ring and a substituent aromatic ring so as not to break the π conjugation. In other words, it is necessary to reduce the dihedral angle between the benzo[c] phenanthrene ring and the substituent aromatic ring.

On the basis of the idea, the sites of substitution on the benzo[c]phenanthrene ring are compared in terms of the dihedral angles between the benzo[c]phenanthrene ring and the substituent aromatic ring. With respect to compounds each substituted with a phenyl group, as an example of the substituent aromatic ring, at a corresponding one of the sites of substitution on the benzo[c]phenanthrene ring, Table 1 shows the results of the dihedral angles between the benzo[c] phenanthrene ring and the benzene ring determined from molecular orbital calculations (B3LYP/6-31G*). Note that for 1-phenyl-substituted compound, the steric interference between the phenyl group and a hydrogen atom at the 12-position is not avoided, so that a stable structure is not obtained.

[Chem. 4]

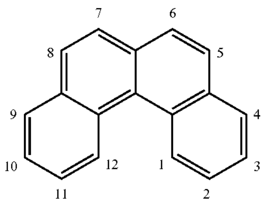

TABLE 1

| | Structural formula | Dihedral angle |
|---|---|---|
| 2-Phenyl-substituted compound | 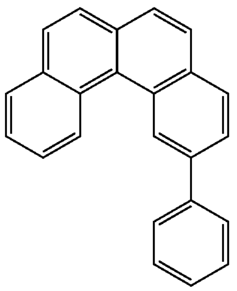 [SMILES: c1ccc(-c2ccc3ccc4ccc5ccccc5c4c3c2)cc1] | 38.1° |

TABLE 1-continued

| | Structural formula | Dihedral angle |
|---|---|---|
| 5-Phenyl-substituted compound | 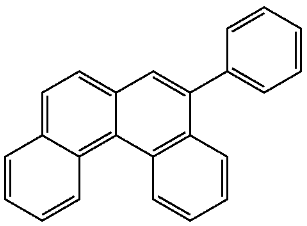 [SMILES: c1ccc(-c2cc3ccc4ccccc4c3c3ccccc23)cc1] | 59.6° |
| 3-Phenyl-substituted compound | 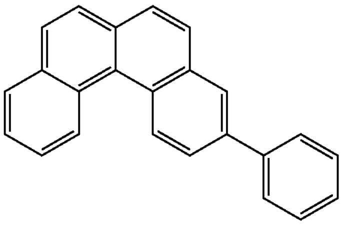 [SMILES: c1ccc(-c2ccc3c(ccc4ccc5ccccc5c43)c2)cc1] | 36.1° |
| 6-Phenyl-substituted compound | 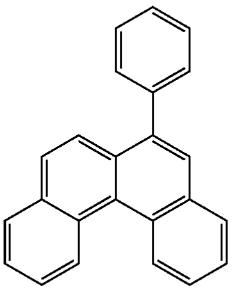 [SMILES: c1ccc(-c2cc3ccccc3c3c2ccc2ccccc23)cc1] | 55.7° |
| 4-Phenyl-substituted compound | 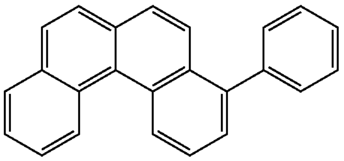 [SMILES: c1ccc(-c2cccc3c2ccc2ccc4ccccc4c23)cc1] | 55.2° |

The results demonstrate that the dihedral angles of 2-phenyl-substituted compound and 3-phenyl-substituted compound in Table 1 are smaller than those of other compounds in Table 1. Thus, the benzo[c]phenanthrene compound, which has a substituent aromatic ring at least at the 2-position or the 3-position, according to aspects of the present invention also has a small dihedral angle between the benzo[c]phenanthrene ring and the substituent aromatic ring. Therefore, the benzo[c]phenanthrene compound according to aspects of the present invention has excellent electron transport properties because the π conjugation extends widely to the aromatic substituent.

Furthermore, the 3-phenyl-substituted compound has a smaller dihedral angle than the 2-phenyl-substituted compound and has the minimum dihedral angle among all sites of substitution. Thus, the substitution to the 3-position results in the maximum extension of the π conjugation, thereby providing the benzo[c]phenanthrene compound having the best electron transport properties. This is because while for the compound substituted at the 2-position, small steric repulsion arises between a hydrogen atom at the α-position of the phenyl substituent and a hydrogen atom at the 12-position of the benzo[c]phenanthrene ring, for the compound substituted at the 3-position, no such steric repulsion arises owing to a sufficient distance therebetween.

To further improve the luminous efficiency of the organic light-emitting device, it is necessary to improve the exciton blocking properties of the electron transport layer. To improve the exciton blocking properties, the energy difference (hereinafter, referred to as an "energy gap") between the HOMO level and the LUMO level of a compound used for the electron transport layer in an amorphous film state may be increased to a value larger than the energy gap of the light-emitting layer.

For the case of a compound having high flatness and containing a wide fused polycyclic ring, e.g., a pyrene ring, in its molecule, the compound shows intermolecular stacking of fused polycyclic rings in an amorphous film state, due to the intermolecular interaction. Thus, the energy gap of the compound is reduced. Accordingly, the use of the electron transport layer containing such a compound reduces the exciton blocking properties.

Meanwhile, the benzo[c]phenanthrene compound according to aspects of the present invention has a large energy gap in an amorphous film state and thus high exciton blocking properties. This is because the low flatness of the benzo[c]phenanthrene ring prevents the formation of the intermolecular stacking in the amorphous film state. The low flatness is attributed to a reduction in the flatness of the ring due to the fact that the ring itself is distorted by the steric repulsion between the hydrogen atoms located at the 1-position and the 12-position of the benzo[c]phenanthrene.

Moreover, in order to enhance the luminous efficiency of the organic light-emitting device, it is necessary to improve the hole blocking properties of the electron transport layer. To improve the hole blocking properties, a compound having a higher ionization potential (deep HOMO level) than that of a material for the light-emitting layer may be used for the electron transport layer. A deeper HOMO level results in a larger effect.

Here, the terms "deep HOMO level" and "deep LUMO level" each indicate that the difference from the vacuum level is large. The terms "low HOMO level" and "low LUMO level" each indicate that the difference from the vacuum level is small.

The benzo[c]phenanthrene compound according to aspects of the present invention has a deep HOMO level and high hole blocking properties compared with those of pyrene compounds and anthracene compounds. This is because the benzo[c]phenanthrene ring at which the HOMO is mainly present is an aromatic ring having a large ionization potential compared with those of pyrene compounds and anthracene compounds.

As described above, the benzo[c]phenanthrene compound according to aspects of the present invention has high chemical stability, high electron transport properties, high exciton blocking properties, and high hole blocking properties. Thus, the use of the electron transport layer composed of the compound results in an organic light-emitting device having high luminous efficiency.

Among the benzo[c]phenanthrene compounds according to aspects of the present invention, compounds represented by formulae [2] and [3] each have a smaller dihedral angle between the benzo[c]phenanthrene ring and the substituent aromatic ring and have high electron transport properties.

[Chem. 5]

[2]

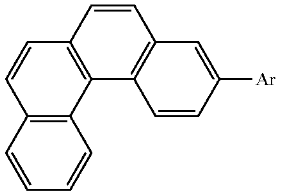

[Chem. 6]

[3]

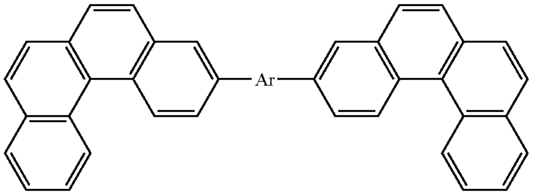

In each of formulae [2] and [3], the substituent, Ar, is as defined for Ar in formula [1].

The benzo[c]phenanthrene compound according to aspects of the present invention may be used for a light-emitting layer of an organic light-emitting device.

The light-emitting layer may consist of the benzo[c]phenanthrene compound according to aspects of the present invention. Alternatively, the benzo[c]phenanthrene compound according to aspects of the present invention may serve as a host material or a guest material. Here, the term "host material" indicates a compound having the highest proportion in weight in the light-emitting layer. The term "guest material" indicates a compound having a lower proportion in weight than that of the host material. Here, the guest material is a compound that is responsible for main light emission in the light-emitting layer. Meanwhile, the host material is a compound which serves as a matrix and which is present around the guest material in the light-emitting layer. The host material is mainly responsible for the transport of carriers and the supply of the guest material with excitation energy.

The concentration of the guest material is in the range of 0.01% by weight to 50% by weight and preferably 0.1% by weight to 20% by weight with respect to the total weight of materials constituting the light-emitting layer. More preferably, in order to prevent concentration quenching, the concentration of the guest material is in the range of 0.01% by weight to 10% by weight. The guest material may be uniformly contained throughout the layer composed of the host material. The guest material may be contained in the light-emitting layer in such a manner that the light-emitting layer has the concentration gradient of the guest material. Alternatively, a region of a host-material layer free from the guest material may be provided by localizing the guest material in a specific region.

In addition to the satisfactory electron transport properties as described above, the benzo[c]phenanthrene compound according to aspects of the present invention also has hole transport properties owing to the main skeleton composed of hydrocarbon and thus can be used as a host material, which is capable of transporting both carriers, for the light-emitting layer. In particular, the benzo[c]phenanthrene compound according to aspects of the present invention can be used as a host material for a blue-light-emitting layer because of the value of its energy gap.

Furthermore, the effect of suppressing the intermolecular stacking as described above also results in the suppression of the exciplex formation between the host material and the guest material and the excimer formation between the host material molecules in the light-emitting layer, thus improving the luminous efficiency of the organic light-emitting device.

Although the benzo[c]phenanthrene compound according to aspects of the present invention has a deep HOMO level, a compound having a relatively shallow HOMO level can be used as the host material for the light-emitting layer. This is because a hole injection barrier caused by the difference in HOMO level between a hole transport layer and the host material for the light-emitting layer is reduced, thus improving the hole injection properties and increasing the luminous efficiency of the device. Among the benzo[c]phenanthrene compounds according to aspects of the present invention, a compound having an aromatic substituent at the 8-position of the benzo[c]phenanthrene ring has a shallow HOMO level compared with an unsubstituted compound and thus can be used as the host material for the light-emitting layer.

Specific examples of the structure of the benzo[c]phenanthrene compound according to aspects of the present invention are illustrated as follows.

[Chem. 7]

101

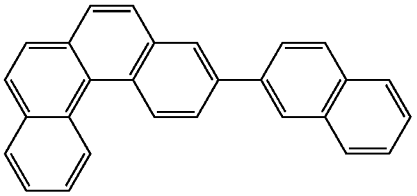

102

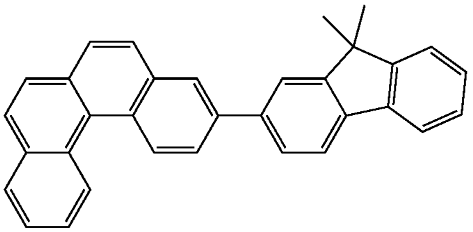

-continued
103
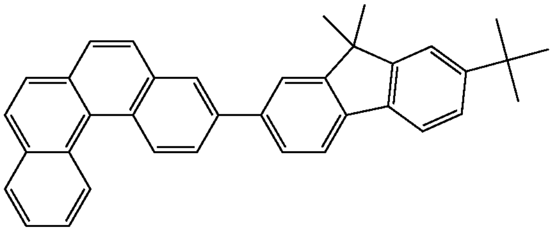
104
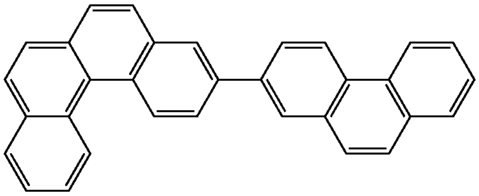
105
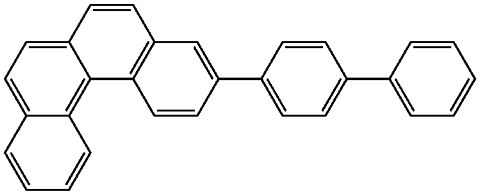
106
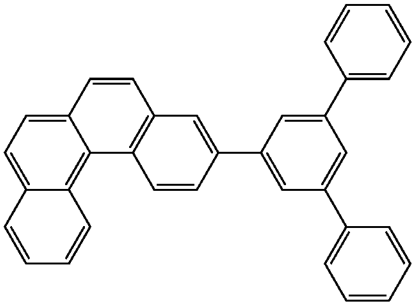
107
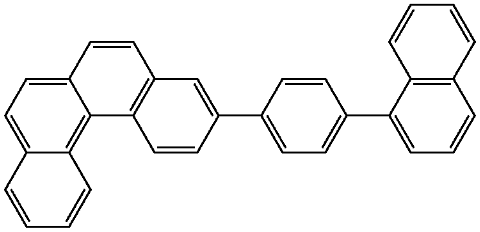
108
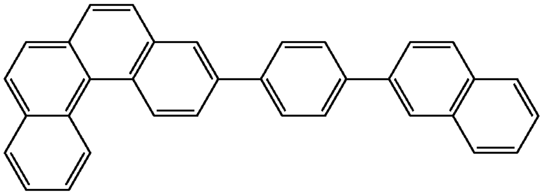
109
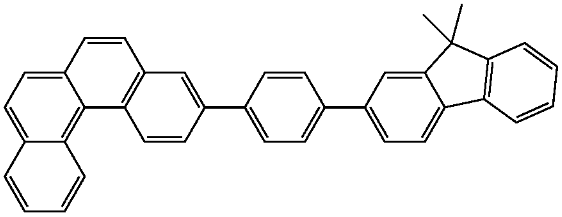
110
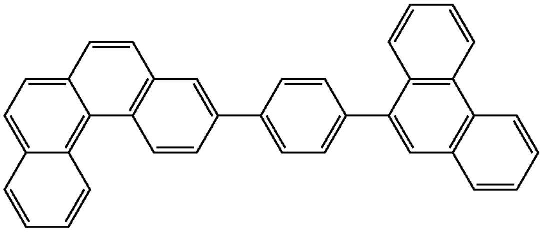
111
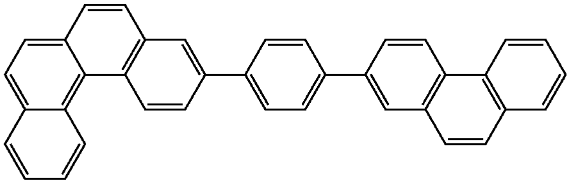
112
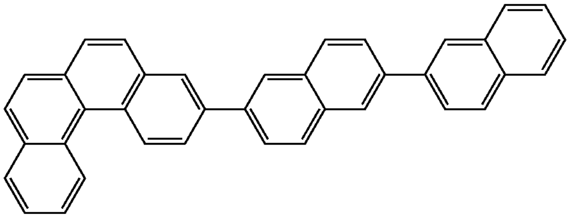
113
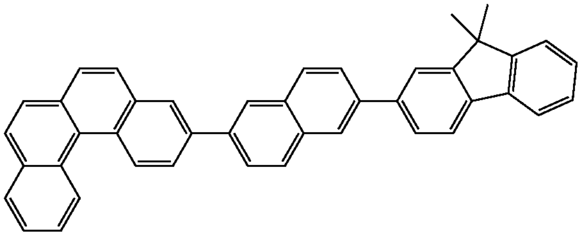
114
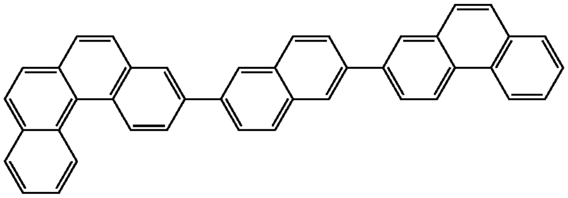

-continued
115
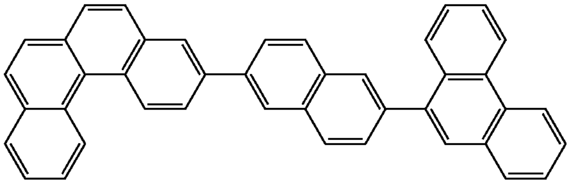
116
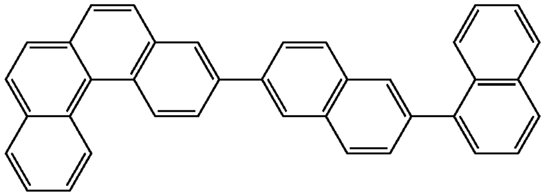
117
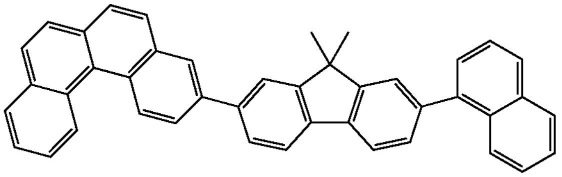
118
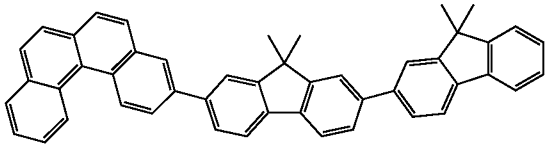
119
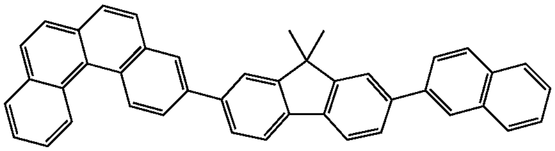
120
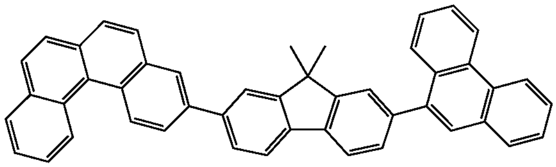
121
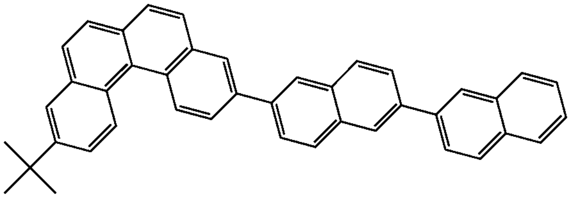
122
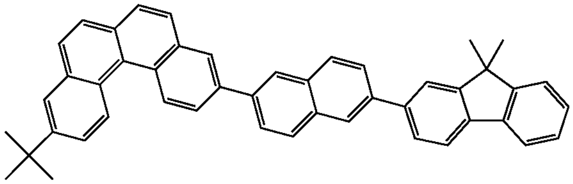
123
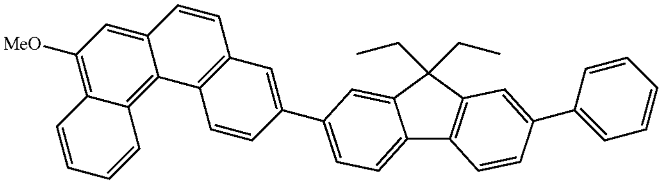
[Chem. 8]
201
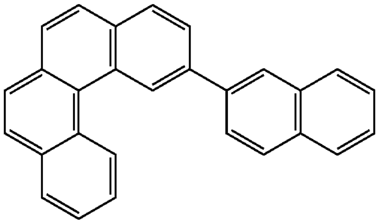
202
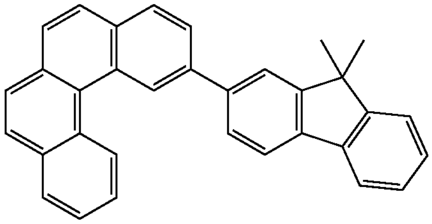
203
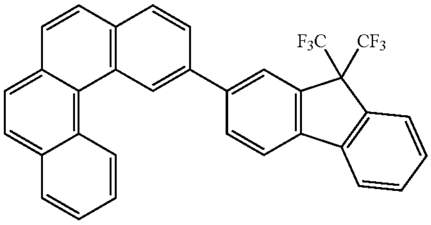
204
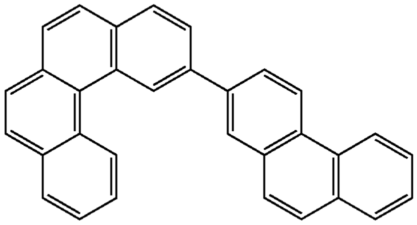

-continued
205
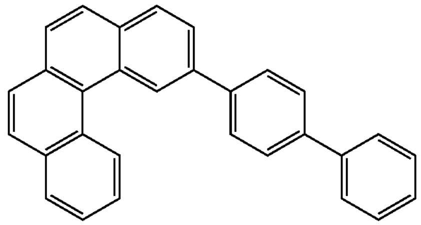
206
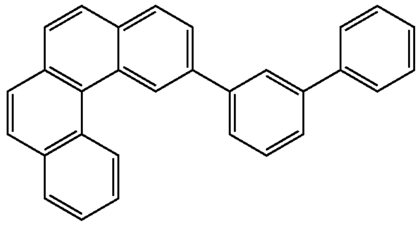
207
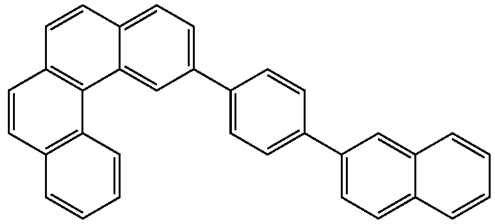
208
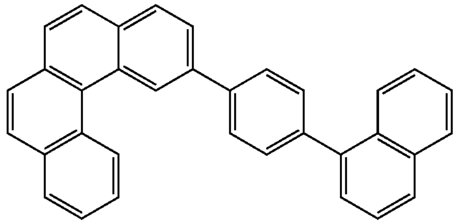
209
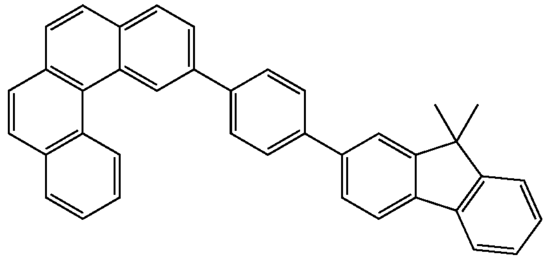
210
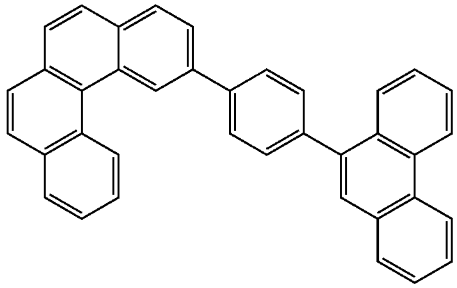
211
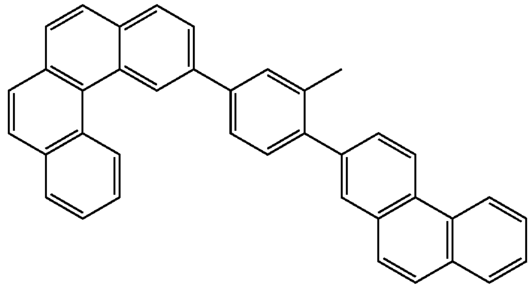
212
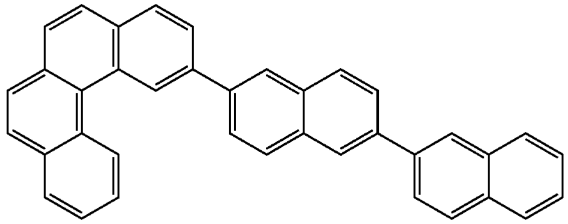
213
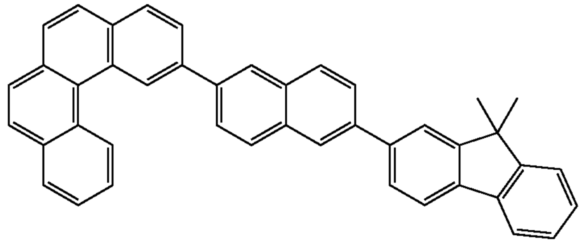
214
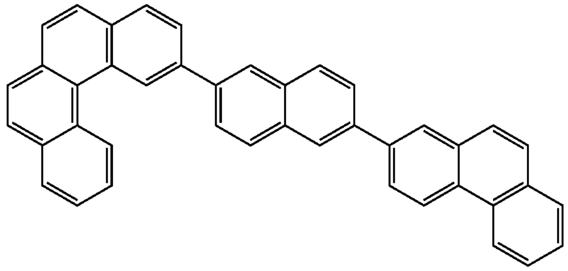

-continued
215
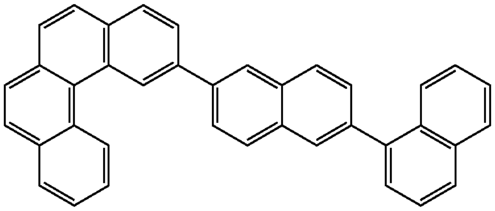
216
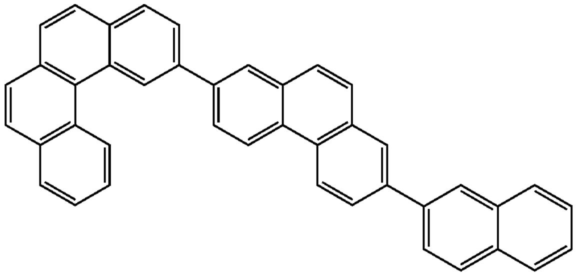
217
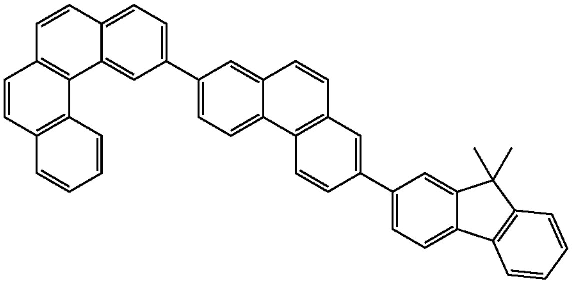
218
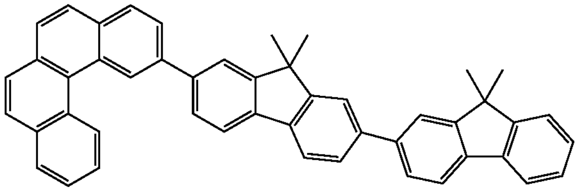
219
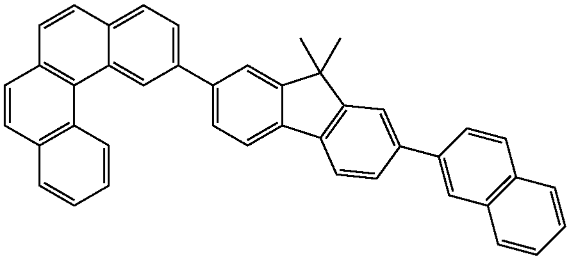
220
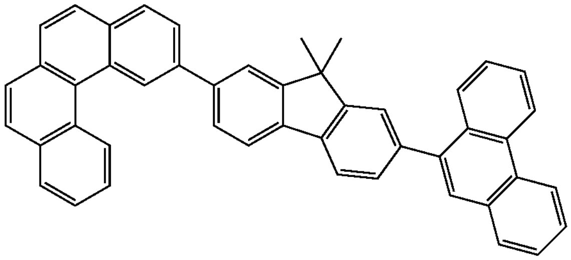
[Chem. 9]
301
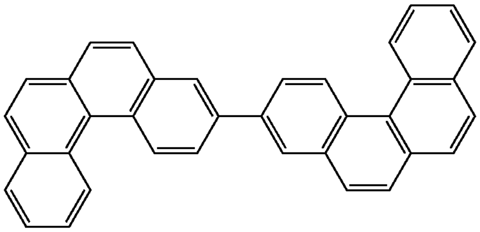
302
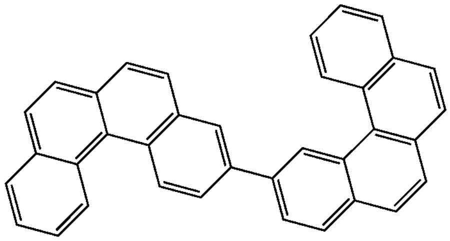
303
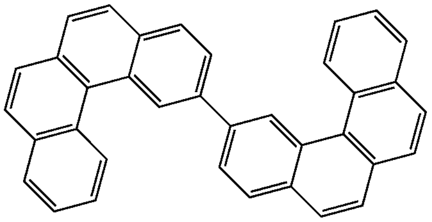
304
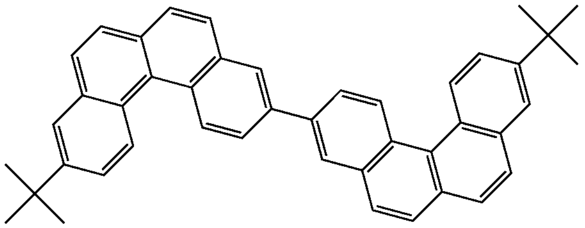

-continued
305
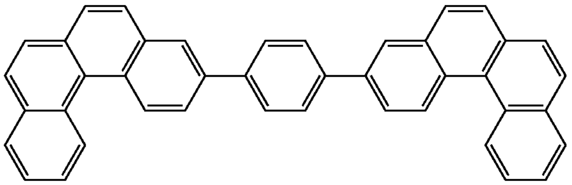
306
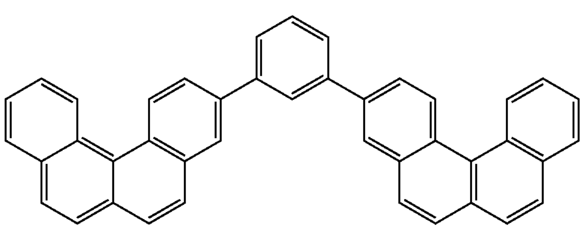
307
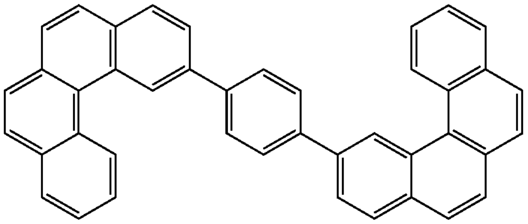
308
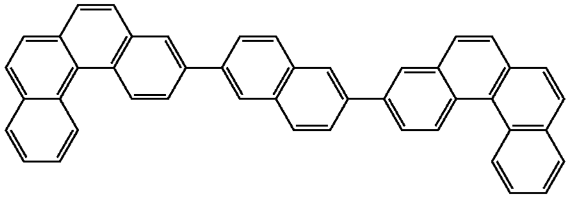
309
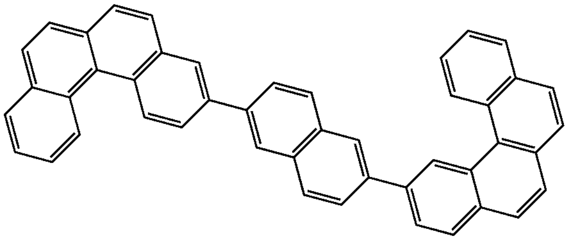
310
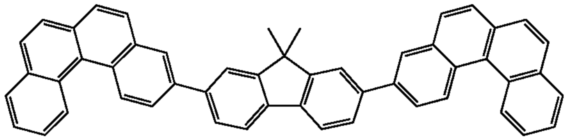
311
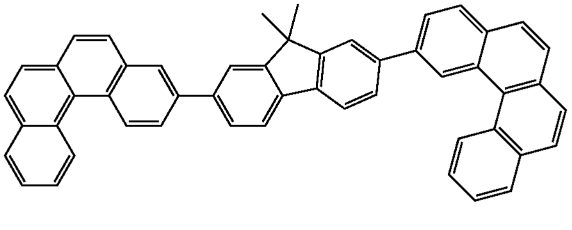
312
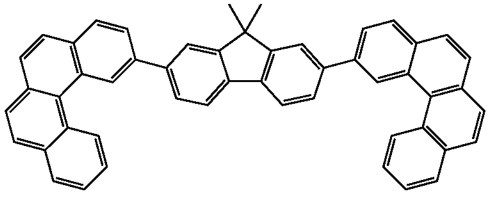
313
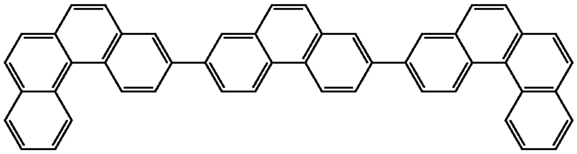
314
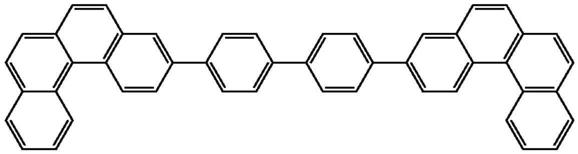

-continued
315
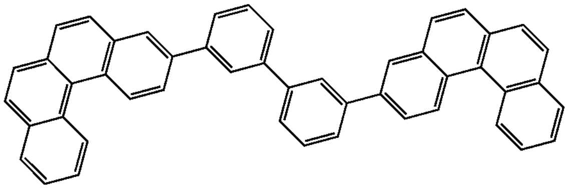
316
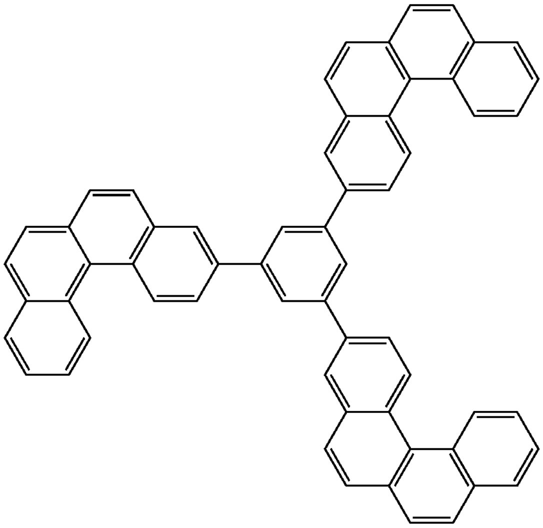
[Chem. 10]
401
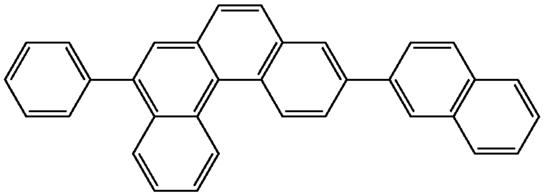
402
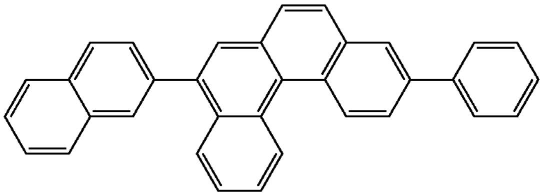
403
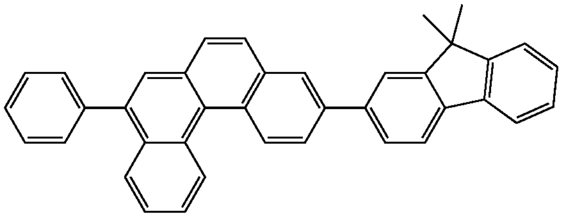
404
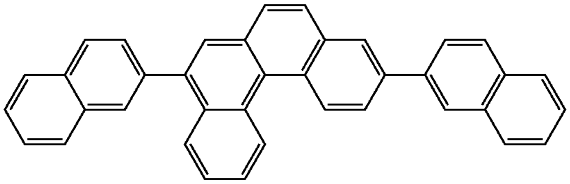
405
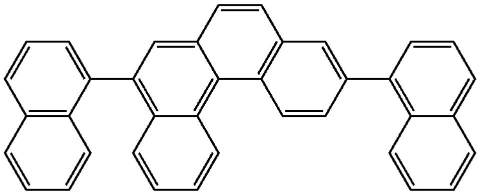
406
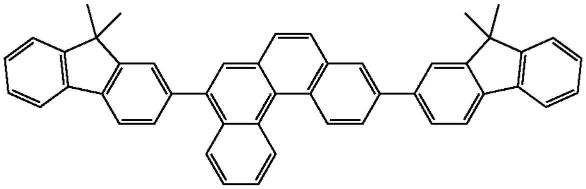
407
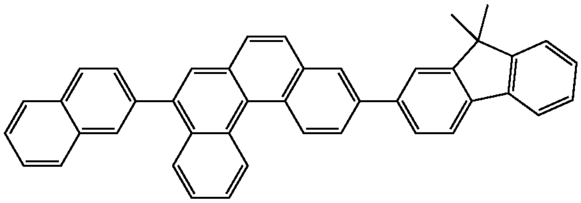
408
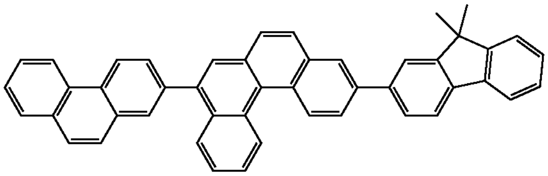

-continued
409
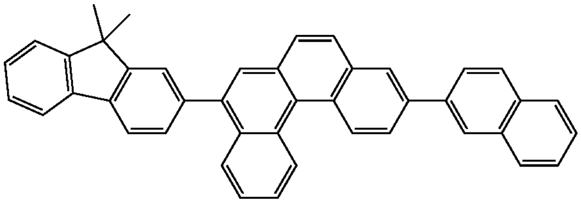
410
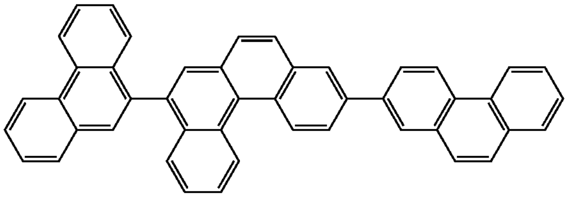
411
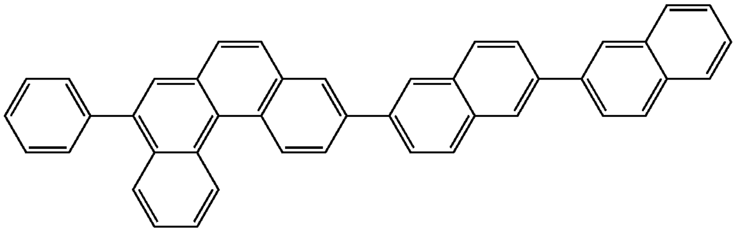
412
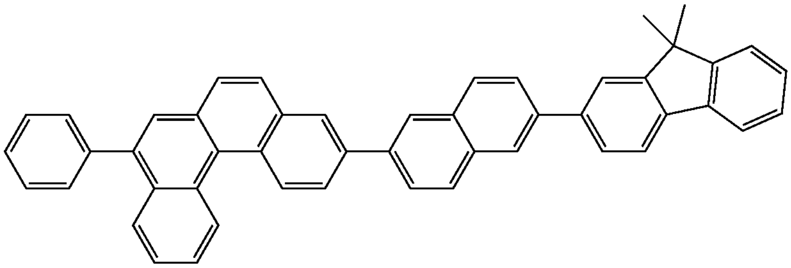
413
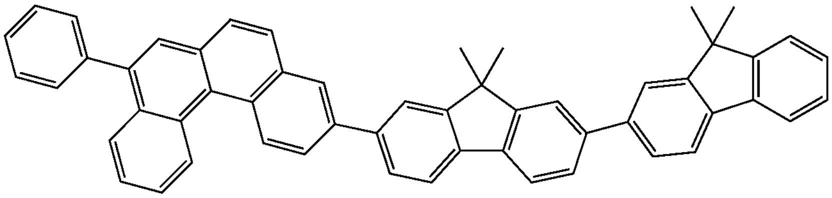
414
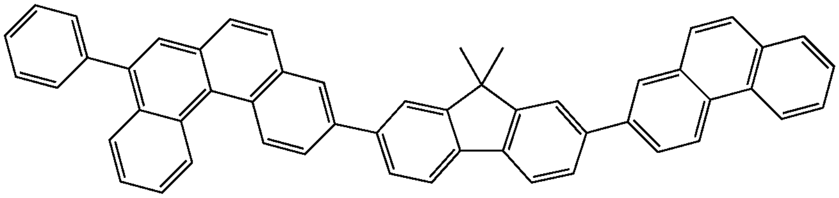
415
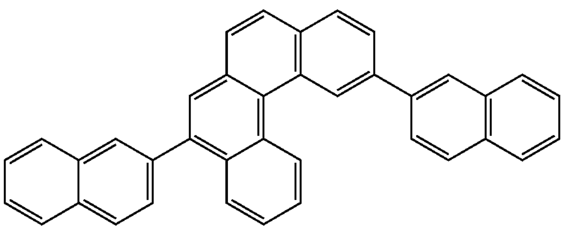
416
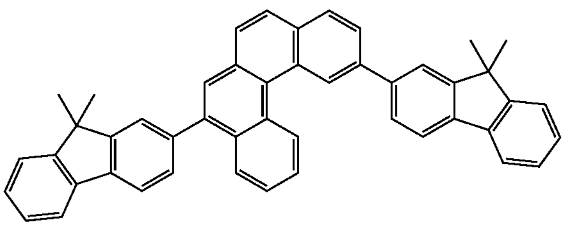

-continued
417
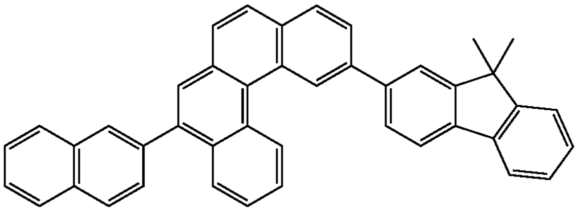
418
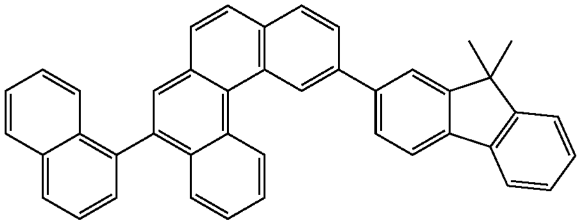
419
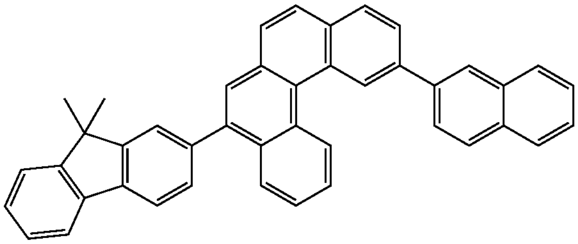
420
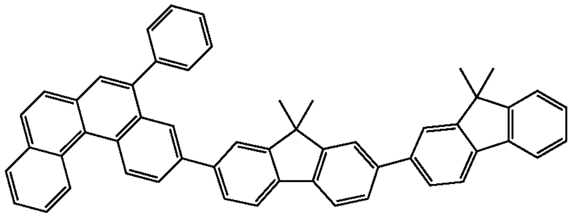
421
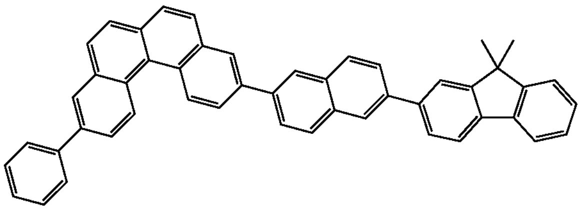
422
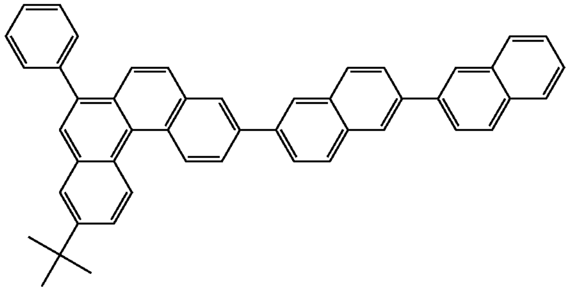
[Chem. 11]
501
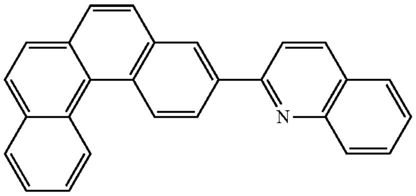
502
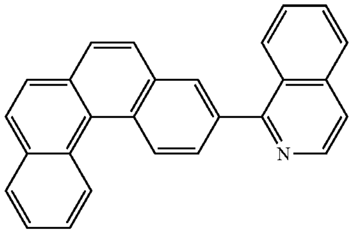
503
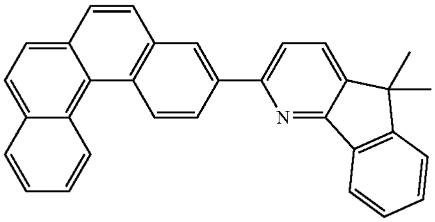
504
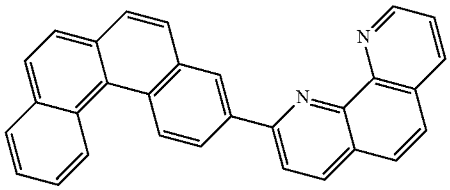

-continued
505
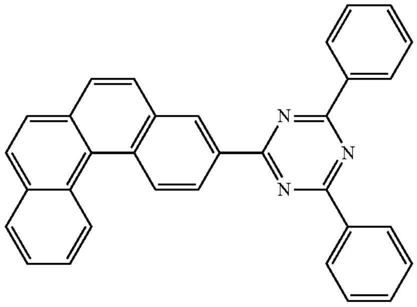
506
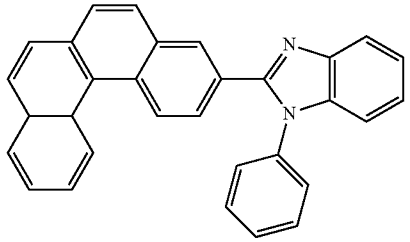
507
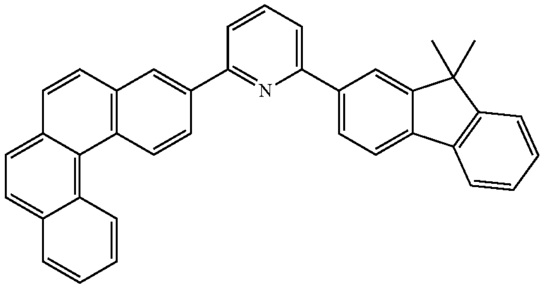
508
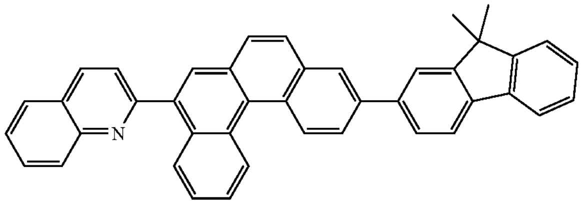
509
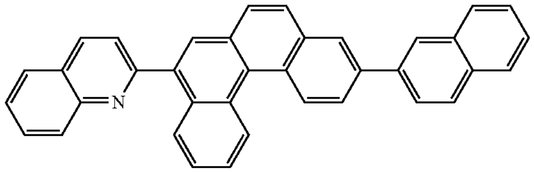
510
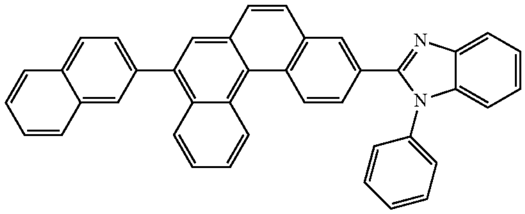
511
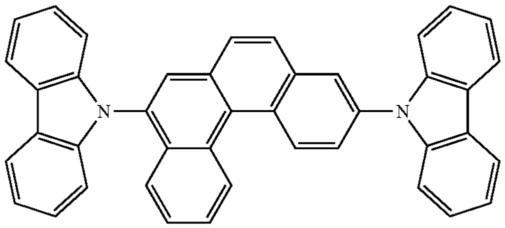
512
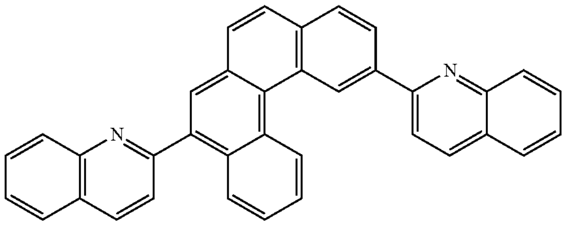
513
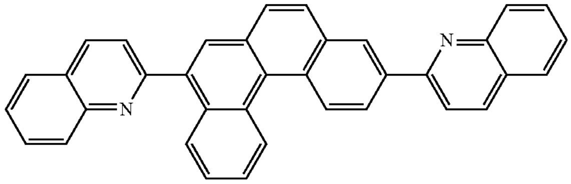
514
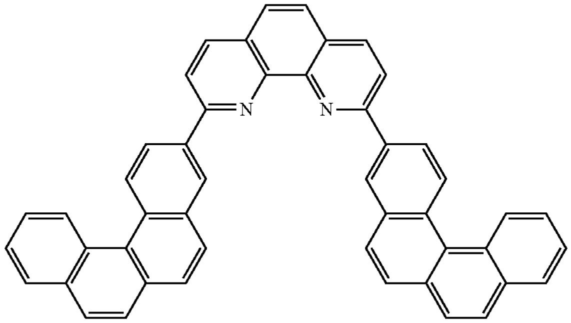

-continued

515

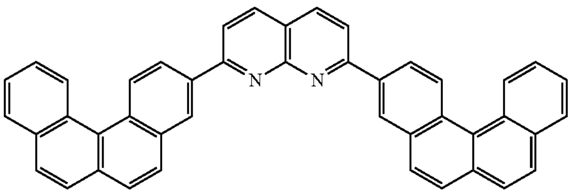

516

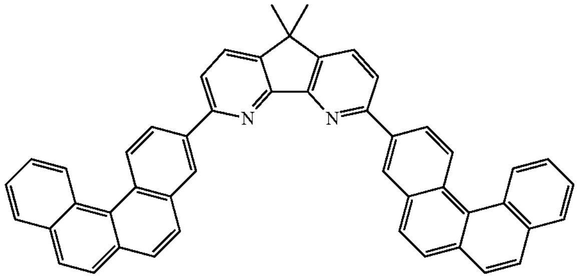

517

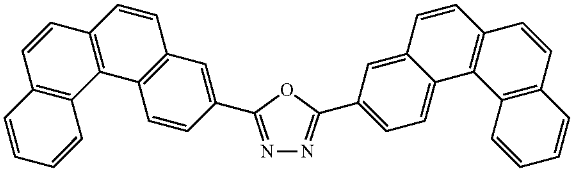

518

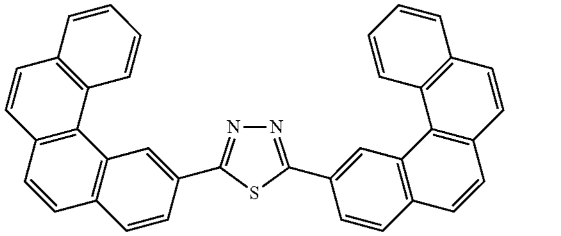

Compounds 101 to 123 (hereinafter, referred to as "100 family") described above are specific examples of compounds each having one aromatic hydrocarbon group at the 3-position of the benzo[c]phenanthrene among the compounds according to aspects of the present invention. These compounds have high electron transport properties, high energy gaps, and deep HOMO levels and thus can be used as the electron transport layer.

Compounds 201 to 220 (hereinafter, referred to as "200 family") described above are specific examples of compounds each having one aromatic hydrocarbon group at the 2-position of the benzo[c]phenanthrene among the compounds according to aspects of the present invention. Similarly to the 100 family, these compounds also have high electron transport properties, high energy gaps, and deep HOMO levels and thus can be used as the electron transport layer.

Compounds 301 to 316 (hereinafter, referred to as "300 family") described above are specific examples of compounds each having two or more benzo[c]phenanthrene rings in its molecule among the compounds according to aspects of the present invention. The compounds of the 300 family have high electron transport properties and deep HOMO levels and thus can be used as the electron transport layer. Furthermore, these compounds have small energy gaps compared with those of the compounds of the 100 family and the 200 family, and thus can be used as the host material for the light-emitting layer.

Compounds 401 to 422 (hereinafter, referred to as "400 family") described above are specific examples of compounds each having the benzo[c]phenanthrene ring including two or more aromatic hydrocarbon groups among the compounds according to aspects of the present invention. Among the compounds of the 400 family, the compounds each having an aromatic substituent at the 8-position of the benzo[c]phenanthrene have shallow HOMO levels and high hole injection properties compared with those of the other exemplified compounds, and thus can be used as the host material for the light-emitting layer.

Compounds 501 to 518 (hereinafter, referred to as "500 family") described above are specific examples of compounds each having the benzo[c]phenanthrene ring including a heteroaromatic group among the compounds according to aspects of the present invention. The compounds of the 500 family have deep HOMO level compared with those of the compounds each having only the aromatic hydrocarbon group, and thus can be used for the electron transport layer.

Methods for synthesizing a 3-aryl-substituted benzo[c]phenanthrene compound and a 3-arylene-substituted benzo[c]phenanthrene compound represented by formulae [2] and [3], respectively, according to this embodiment will be described below.

The 3-aryl-substituted benzo[c]phenanthrene compound can be synthesized from a 3-Cl raw material or a 3-Bpin raw material by the Suzuki-Miyaura coupling reaction represented by formula [4]:

[Chem. 12]

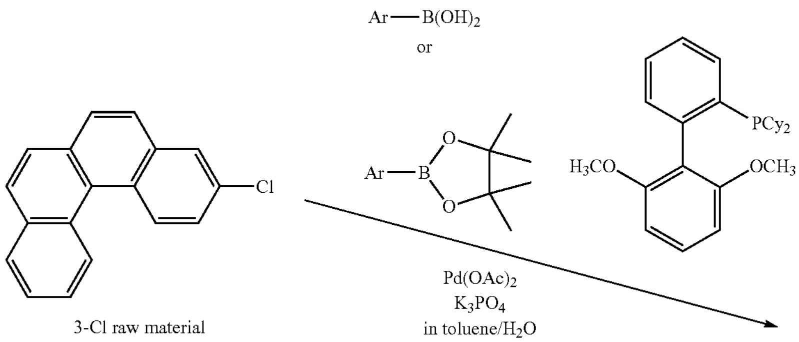

3-Cl raw material

-continued

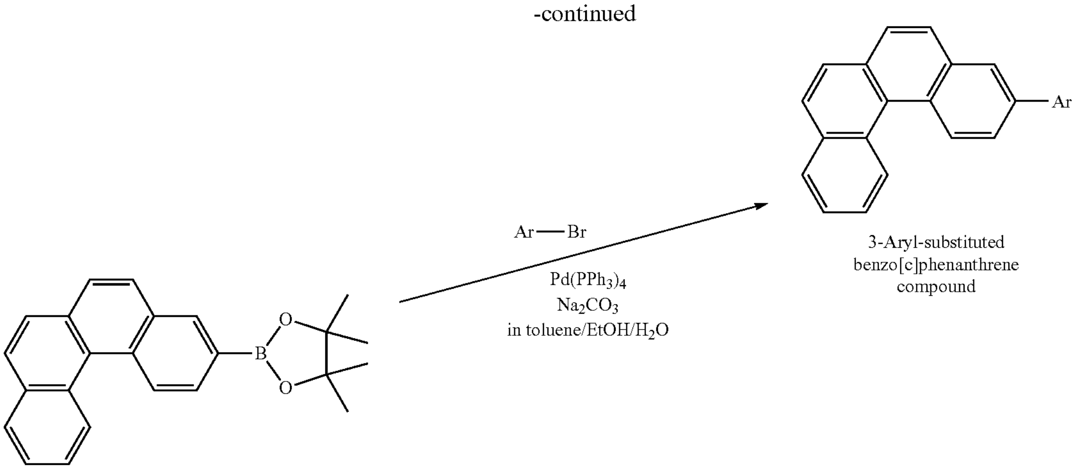

[4]

3-Bpin raw material

3-Aryl-substituted benzo[c]phenanthrene compound wherein Ar represents a substituted or unsubstituted aromatic hydrocarbon group or a substituted or unsubstituted heteroaromatic group.

Similarly, the 3-arylene-substituted benzo[c]phenanthrene compound can be synthesized from the 3-Cl raw material or the 3-Bpin raw material as illustrated in formula [5]:

[Chem. 13]

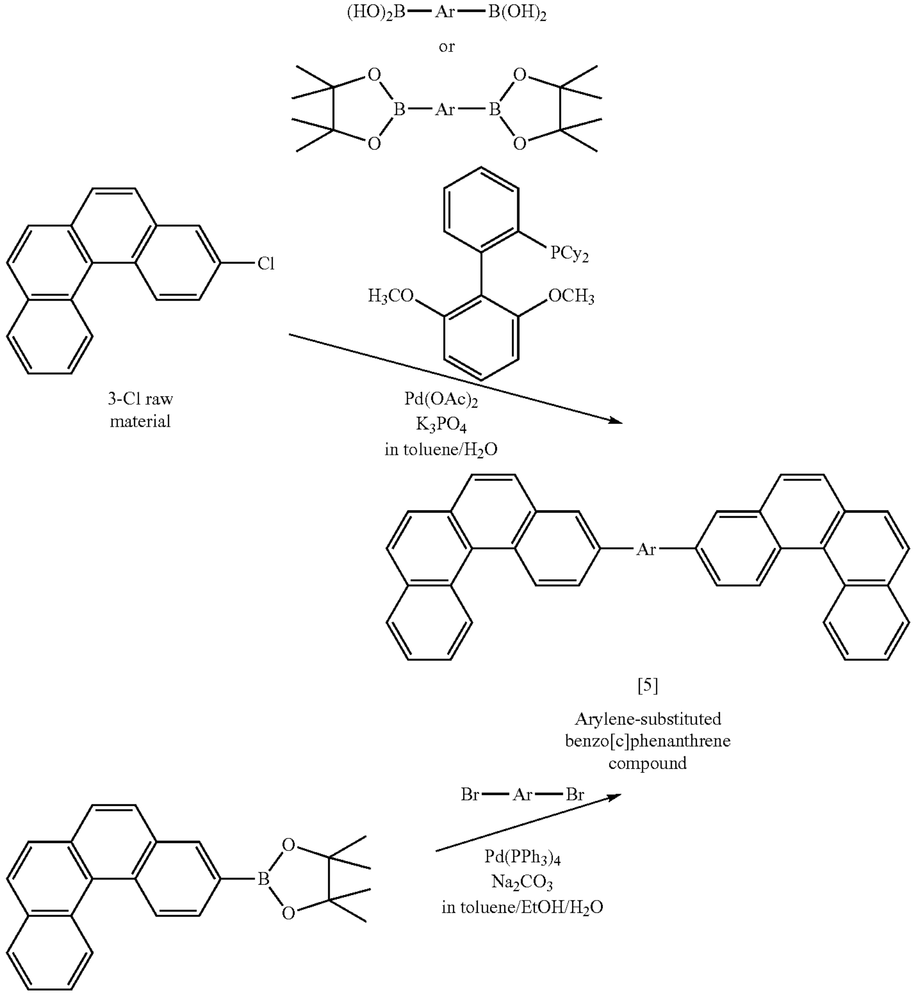

3-Cl raw material

[5]

Arylene-substituted benzo[c]phenanthrene compound

3-Bpin raw material wherein Ar represents a substituted or unsubstituted aromatic hydrocarbon group or a substituted or unsubstituted heteroaromatic group.

In each of formulae [4] and [5], the benzo[c]phenanthrene compound substituted with a desired Ar group can be synthesized by introducing the desired Ar group as Ar. In this case, as a halogen compound or a boronic acid compound in each of the formulae, a halogen compound or a boronic acid compound corresponding to the desired Ar group may be used in the reaction.

In the case where an alkyl group, an alkoxy group, an aromatic hydrocarbon group, or a heteroaromatic group is introduced into the benzo[c]phenanthrene compound, which is the final compound in each of the formulae, at a position other than the 3-position of the benzo[c]phenanthrene ring, the 3-Cl raw material or the 3-Bpin raw material in each of the formulae may be substituted with the corresponding substituent.

Furthermore, 2-aryl-substituted benzo[c]phenanthrene compound and 2-arylene-substituted benzo[c]phenanthrene compound can also be synthesized by the Suzuki-Miyaura coupling reaction. That is, in each of formulae [4] and [5], the synthesis may be conducted using 2-chlorobenzo[c]phenanthrene as a synthetic raw material.

An organic light-emitting device according to aspects of the present invention will be described in detail below.

The organic light-emitting device according to aspects of the present invention includes a pair of electrodes and an organic compound layer provided between the pair of electrodes, in which the organic compound layer contains the benzo[c]phenanthrene compound represented by formula [1].

An example of the organic light-emitting device containing the benzo[c]phenanthrene compound according to aspects of the present invention will be described below.

The organic light-emitting device according to aspects of the present invention may have a structure in which a light-emitting layer is provided between an anode and a cathode, which are an example of the pair of electrodes. Furthermore, the organic light-emitting device may include a hole transport layer and a hole injection layer between the anode and the light-emitting layer. Moreover, the organic light-emitting device may include an electron transport layer, an electron injection layer, a hole/exciton blocking layer, and so forth between the light-emitting layer and the cathode. The layer structure of the organic compound layer of the light-emitting device containing the compound according to aspects of the present invention is not limited thereto.

For the organic light-emitting device according to aspects of the present invention, the organic compound layer may include a plurality of layers. Examples of the plural layers include the hole injection layer, the hole transport layer, the light-emitting layer, a hole blocking layer, an exciton blocking layer, the electron transport layer, and the electron injection layer. These layers may be appropriately used in combination.

The benzo[c]phenanthrene compound according to aspects of the present invention can be used for the electron transport layer.

Furthermore, the benzo[c]phenanthrene compound according to aspects of the present invention may be used for layers other than the electron transport layer, i.e., may be used for any of the hole injection layer, the hole transport layer, the light-emitting layer, the hole blocking layer, the exciton blocking layer, and the electron injection layer. In particular, the benzo[c]phenanthrene compound according to aspects of the present invention can be used as the host material for the light-emitting layer. In the case where the benzo[c]phenanthrene compound according to aspects of the present invention is used in the electron injection layer, the electron injection layer may be doped with a reducing dopant such as an alkali metal in order to improve electron injection properties from the cathode.

Here, the organic light-emitting device according to aspects of the present invention may contain the benzo[c]phenanthrene compound according to aspects of the present invention together with a known compound, for example, a low-molecular-weight hole transport compound, a high-molecular-weight hole transport compound, a light-emitting compound, or an electron transport compound, as needed.

Examples of these compounds are described below.

As a hole injection/transport material, a material having a high hole mobility can be used from the viewpoint of achieving easy hole injection from the anode and transporting the injected holes to the light-emitting layer. Examples of a low-molecular-weight material and a polymer material having hole injection/transport properties include triarylamine derivatives, phenylenediamine derivatives, stilbene derivatives, phthalocyanine derivatives, porphyrin derivatives, poly(vinylcarbazole), polythiophene, and other conductive polymers.

Examples of a light-emitting material participating mainly in a light-emitting function include fused-ring compounds (e.g., fluorene derivatives, naphthalene derivatives, pyrene derivatives, perylene derivatives, tetracene derivatives, anthracene derivatives, rubrene derivatives, fluoranthene derivatives, and benzofluoranthene derivatives), quinacridone derivatives, coumarin derivatives, stilbene derivatives, organic aluminum complexes such as tris(8-quinolinolato) aluminum, organic beryllium complexes, polymer derivatives, such as poly(phenylenevinylene) derivatives, polyfluorene derivatives, polyphenylene derivatives, and phosphorescent iridium complexes and platinum complexes.

Any material into which electrons can be easily injected from the cathode and which can transport the injected electrons to the light-emitting layer can be used as an electron injection/transport material. The electron injection/transport material is selected in view of, for example, the hole mobility of the hole injection/transport material. Examples of a material having the electron injection/transport properties include oxadiazole derivatives, oxazole derivatives, pyrazine derivatives, triazole derivatives, triazine derivatives, quinoline derivatives, quinoxaline derivatives, phenanthroline derivatives, and organic aluminum complexes.

The anode may be composed of a material having a higher work function. Examples of the material that can be used include elemental metals, such as gold, platinum, silver, copper, nickel, palladium, cobalt, selenium, vanadium, and tungsten; alloys thereof; and metal oxides, such as tin oxide, zinc oxide, indium oxide, indium tin oxide (ITO), and indium zinc oxide. Furthermore, conductive polymers, such as polyaniline, polypyrrole, polythiophene, and poly(phenylene sulfide), may be used. These materials for the electrode may be used alone or in combination. The anode may be formed of a single layer or multiple layers.

The cathode may be composed of a material having a lower work function. Examples of the material include elemental metals, such as alkali metals, e.g., lithium, alkaline-earth meals, e.g., calcium, aluminum, titanium, manganese, silver, lead, and chromium; and alloys thereof. Examples of the alloys that can be used include magnesium-silver, aluminum-lithium, and aluminum-magnesium. Metal oxides such as indium tin oxide (ITO) may be used. These materials for the electrode may be used alone or in combination. The cathode may be formed of a single layer or multiple layers.

Examples of the substrate used in the organic light-emitting device according to aspects of the present invention include, but are not particularly limited to, opaque substrates, such as metallic substrates and ceramic substrates; and transparent substrates, such as glass substrates, quartz substrates, and plastic sheets. Furthermore, it is also possible to control the emission color using a color filter film, a fluorescent color conversion filter film, a dielectric reflection film, or the like on the substrate.

In order to prevent contact with oxygen, water, and so forth, a protective layer or a sealing layer may be arranged on the resulting device. Examples of the protective layer include diamond thin films, inorganic films composed of inorganic substances, such as metal oxides and metal nitride; polymeric films composed of polymers, such as fluorinated resins, polyethylene, silicone resins, and polystyrene resins; and photocurable resins. Furthermore, the device may be covered with, for example, glass, a gas-impermeable film, or a metal, and packaged in an appropriate sealing resin.

With respect to the direction of light emission of the device, the organic light-emitting device according to aspects of the present invention may have a bottom-emission structure, in which light emerges from the substrate, or a top-emission structure, in which light emerges from a surface opposite the substrate.

In the organic light-emitting device according to aspects of the present invention, a layer containing the benzo[c]phenanthrene compound according to aspects of the present invention and another layer composed of an organic compound are formed by a method described below. Specifically, an organic compound layer may be formed by vacuum evaporation, ionized evaporation, sputtering, or a method using plasma. Alternatively, an organic compound layer may be formed by a coating method, e.g., spin coating, dipping, casting, the Langmuir-Blodgett (LB) technique, or an ink-jet method, using a solution of a material dissolved in an appropriate solvent. Here, the formation of the layer by, for example, vacuum evaporation or the coating method, is less likely to cause crystallization or the like, resulting in excellent stability with time. Furthermore, in the case of forming a film by a coating method, the film may be formed in combination with an appropriate binder resin.

The organic light-emitting device according to aspects of the present invention may be used for, for example, a display, lighting apparatuses, an exposing light source of an image forming apparatus using an electrographic method, or a backlight of a liquid crystal display.

The display is provided with a display unit that includes the organic light-emitting device according to aspects of the present invention. The display unit includes a plurality of pixels. Each of the pixels includes the organic light-emitting device according to aspects of the present invention and a TFT element as an example of a switching element. The anode or cathode of the organic light-emitting device is connected to a drain electrode or a source electrode of the TFT element. The display may be used as an image display apparatus of, for example, a personal computer.

The display may be used for a display unit of an image pick-up apparatus, for example, a digital camera or a digital video camera. The image pick-up apparatus includes the display unit and an image pick-up unit configured to pick-up an image, the image pick-up unit including an image pick-up optical system such as a lens. The display may be used not only for the display unit of the image pick-up apparatus but also a display unit of an ink-jet printer.

The display may be an image input device that includes an image input unit configured to input information from, for example, an area CCD sensor, a linear CCD sensor, or a memory card. Furthermore, the display may have both functions: as a display unit included in an image pick-up apparatus or an ink-jet printer, an image output function that displays an image on the basis of image information supplied from the outside; and as an operation panel, an input function that inputs processing information to an image. Furthermore, the display may be used for a display unit of a multifunction printer. Next, the display including the organic light-emitting device according to aspects of the present invention will be described.

FIG. 1 is a cross-sectional view illustrating organic light-emitting devices according to aspects of the present invention and TFT elements, which are exemplary switching elements that switch between emission and non-emission of light from the organic light-emitting device. In this figure, two organic light-emitting devices and two TFT elements are illustrated. The structure will be described in detail below.

A display illustrated in FIG. 1 includes a substrate 1 composed of, for example, glass, and a dampproofing film 2 formed on the substrate 1, the dampproofing film 2 being configured to protect the TFT elements or the organic compound layers. Reference numeral 3 denotes a gate electrode. Reference numeral 4 denotes a gate insulating film. Reference numeral 5 denotes a semiconductor layer.

TFT elements 8 each include the semiconductor layer 5, a drain electrode 6, and a source electrode 7. The TFT elements 8 are overlaid with an insulating film 9. An anode 11 of each organic light-emitting device is connected to a corresponding one of the source electrodes 7 through a corresponding one of contact holes 10. The display is not limited to this structure as long as one of the anode and the cathode is connected to one of the source electrode and the drain electrode of each TFT element.

Although organic compound layers 12 each have a multilayer structure, each of the organic compound layers 12 is illustrated as a single layer. Cathodes 13 are overlaid with a first protective layer 14 and a second protective layer 15 configured to suppress the degradation of the organic light-emitting device.

In the display according to aspects of the present invention, the switching element is not particularly limited. For example, a single-crystal silicon substrate, an MIM element, an a-Si element may be used.

EXAMPLES

Example 1

Synthesis of Exemplary Compound 113

(1) Synthesis of 3-Cl Raw Material

[Chem. 14]

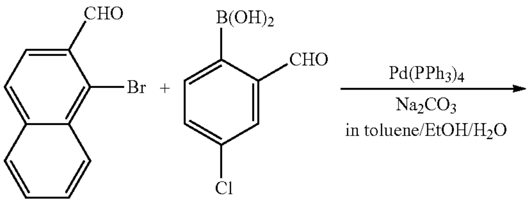

-continued

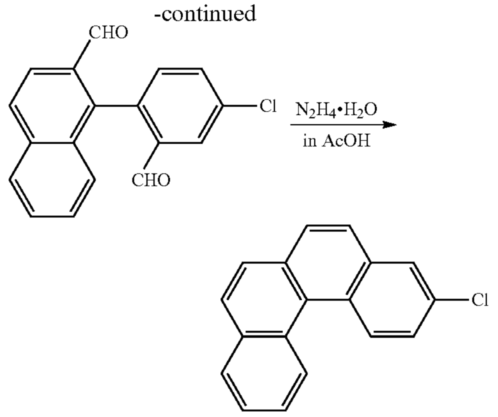

3-Cl raw material

Reagents and solvents described below were charged into a 200-mL recovery flask.

1-Bromo-2-naphthaldehyde: 2.00 g (8.51 mmol)

4-Chloro-2-formylphenylboronic acid: 1.65 g (8.93 mmol)

Tetrakis(triphenylphosphine)palladium(0): 0.29 g (0.26 mmol)

Toluene: 60 mL

Ethanol: 30 mL

Aqueous solution of 10% by weight sodium carbonate: 30 mL

The resulting reaction mixture was heated to reflux for 4.5 hours with stirring under nitrogen. After the completion of the reaction, the reaction solution was washed with water, dried over sodium sulfate, and concentrated to give a crude product. The crude product was then purified by silica gel column chromatography (eluent: toluene/heptane=8/1) to give 1.95 g (yield: 78%) of oily 1-(4-chloro-2-formylphenyl)-2-naphthaldehyde.

Subsequently, the reagent and a solvent described below were charged into a 300-mL three-necked flask equipped with a dropping funnel.

1-(4-Chloro-2-formylphenyl)-2-naphthaldehyde: 1.95 g (6.63 mmol)

Acetic acid: 115 mL

The resulting reaction solution was heated to reflux with stirring under nitrogen. A solution of 10 mL of acetic acid and 0.44 g (8.61 mmol) of hydrazine monohydrate was added dropwise over a period of 5 minutes from the dropping funnel to the reaction solution. After the completion of the dropwise addition, the reflux was continued for another 3 hours. After the completion of the reaction, the acetic acid solvent was removed by evaporation to concentrate the solution. Extraction was performed with diethyl ether. The resulting extract was washed with water, dried over sodium sulfate, and further concentrated to give a crude product. The crude product was purified by silica gel column chromatography (eluent: heptane/chloroform=4/1) and then recrystallized from methanol to give 1.24 g (yield: 71%) of a 3-Cl raw material (3-chlorobenzo[c]phenanthrene).

The resulting compound was identified by $^1$H-NMR measurement.

[$^1$H-NMR (400 MHz, $CDCl_3$)]

δ 9.05 (d, 1H), 9.03 (d, 1H), 8.03 (dd, 1H), 8.00 (dd, 1H), 7.96-7.75 (m, 4H), 7.75-7.55 (m, 3H).

(2) Synthesis of 3-Bpin Raw Material

[Chem. 15]

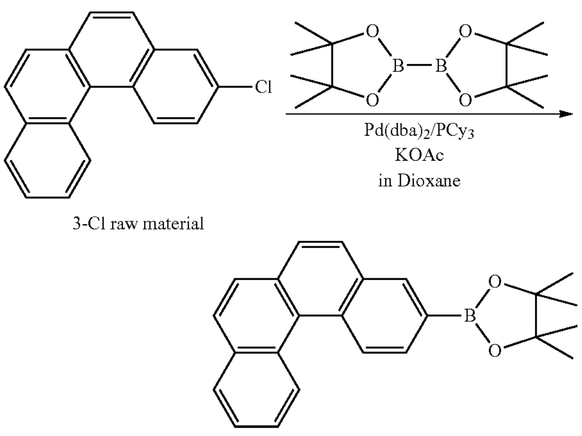

Reagents and a solvent described below were charged into a 50-mL three-necked flask.

3-Cl raw material: 713 mg (2.71 mmol)

Bis(pinacolato)diboron: 830 g (3.27 mmol)

Bis(dibenzylideneacetone)palladium(0): 153 mg (0.27 mmol)

Tricyclohexylphosphine: 196 mg (0.67 mmol)

Potassium acetate: 800 mg (8.15 mmol)

1,4-Dioxane: 21 mL

The resulting reaction mixture was stirred at 90° C. for 12 hours under nitrogen. After the completion of the reaction, the reaction solution was washed with water, dried over sodium sulfate, and concentrated to give a crude product. The crude product was then purified by silica gel column chromatography (eluent: heptane/toluene=1/1) to give 306 mg (yield: 32%) of a 3-Bpin material.

(3) Synthesis of Exemplary Compound 113

[Chem. 16]

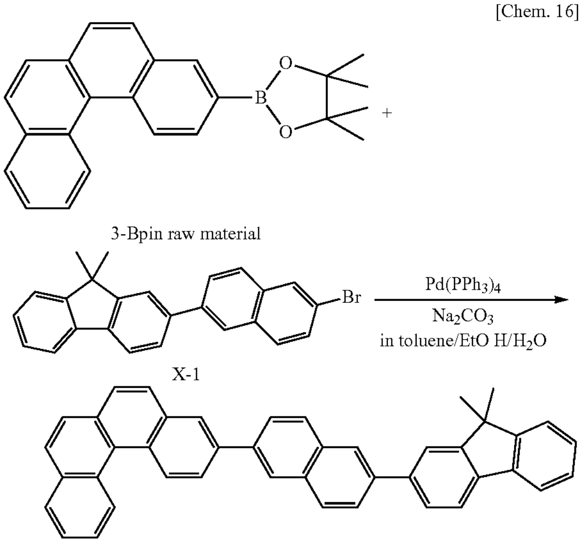

Exemplified compound 113

Reagents and solvents described below were charged into a 50-mL recovery flask.

3-Bpin raw material: 263 mg (0.74 mmol)

Halogen compound X-1: 311 mg (0.78 mmol)

Tetrakis(triphenylphosphine)palladium(0): 43 mg (37 μmol)

Toluene: 10 mL

Ethanol: 5 mL

Aqueous solution of 10% by weight sodium carbonate: 5 mL

The resulting reaction mixture was heated to reflux for 5 hours with stirring under nitrogen. After the completion of the reaction, water and ethanol were added to the reaction solution. The resulting mixture was stirred to precipitate a product. The precipitated product was filtered to give a gray powder as a crude product. The crude product was dissolved in heated toluene. The solution was passed through a short silica gel column to remove the residual catalyst. Recrystallization purification was performed twice from a toluene/heptane mixed solvent and then chloroform/ethanol mixed solvent. The resulting crystals were dried at 150° C. under vacuum and then subjected to sublimation purification at $10^{-4}$ Pa and 330° C. to give 122 mg (yield: 30%) of exemplary compound 113.

The identification results of the resulting compound were described below.

[Matrix-assisted laser desorption ionization-time-of-flight mass spectrometry (MALDI-TOF-MS)]

Observed value: m/z=546.21, calculated value: $C_{43}H_{30}$=546.23

[$^1$H-NMR (400 MHz, $CDCl_3$)]

δ 9.26 (d, 1H), 9.20 (d, 1H), 8.40 (s, 1H), 8.32 (s, 1H), 8.23-7.54 (m, 17H), 7.54-7.30 (m, 3H), 1.60 (s, 6H).

The energy gap of exemplary compound 113 was measured by a method described below.

Exemplary compound 113 was deposited on a glass substrate by thermal evaporation to form a deposited thin film having a thickness of 20 nm. The absorption spectrum of the deposited thin film was measured with an ultraviolet and visible spectrophotometer (Model V-560, manufactured by JASCO Corporation). The absorption edge of the resulting absorption spectrum was determined and found to be 407 nm. Exemplary compound 113 had an energy gap of 3.05 eV.

Furthermore, the ionization potential of exemplary compound 113 was measured by a method described below.

Exemplary compound 113 was deposited on a glass substrate by thermal evaporation to form a deposited thin film having a thickness of 20 nm. The ionization potential of the deposited thin film was measured with a photoelectron spectrometer (Model AC-2, manufactured by Riken Keiki Co., Ltd). The results of the measurement demonstrated that exemplary compound 113 had an ionization potential of 5.82 eV.

Example 2

Synthesis of Exemplary Compound 118

[Chem. 17]

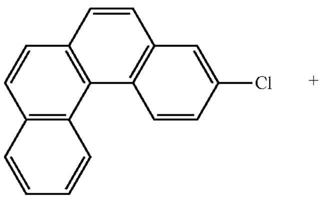

3-Cl raw material

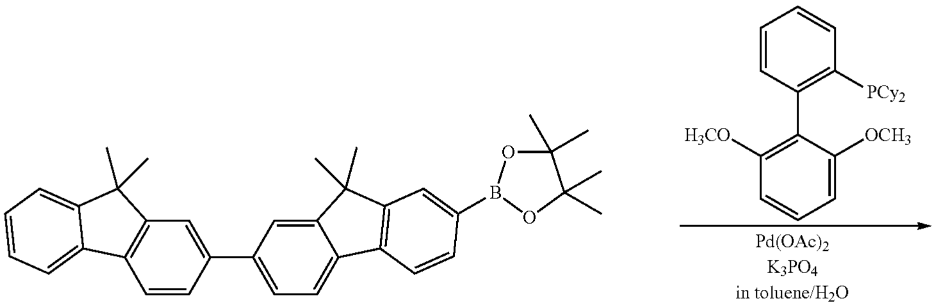

BO-1

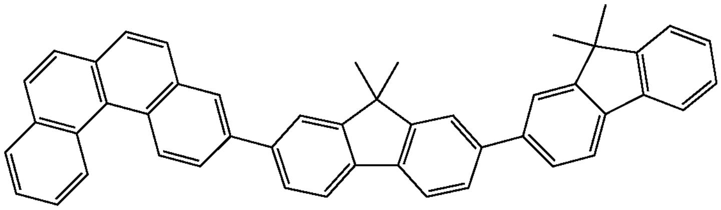

Exemplified compound 118

Reagents and solvents described below were charged into a 50-mL recovery flask.

3-Cl raw material: 400 mg (1.52 mmol)
Boronic acid compound BO-1: 819 mg (1.60 mmol)
Palladium(II) acetate: 34 mg (152 μmol)
2-Dicyclohexylphosphino-2',6'-dimethoxybiphenyl: 156 mg (381 μmol)
Potassium phosphate: 0.97 g (4.57 mmol)
Toluene: 20 mL
Water: 0.5 mL The resulting reaction mixture was stirred for 4.5 hours at 100° C. under nitrogen. After the completion of the reaction, water was added to the reaction mixture. The resulting mixture was stirred to precipitate a product. The precipitated product was filtered to give a gray powder as a crude product. The crude product was dissolved in heated toluene. The solution was passed through a short silica gel column to remove the residual catalyst. Recrystallization purification was performed from a toluene/octane mixed solvent. The resulting crystals were dried at 150° C. under vacuum and then subjected to sublimation purification at $10^{-4}$ Pa and 345° C. to give 518 mg (yield: 56%) of high-purity exemplary compound 118.

The identification results of the resulting compound were described below.

[MALDI-TOF-MS]

Observed value: m/z=612.35, calculated value: $C_{48}H_{36}$=612.28

[$^1$H-NMR (400 MHz, $CDCl_3$)]

δ 9.24 (d, 1H), 9.19 (d, 1H), 8.32 (s, 1H), 8.15-7.95 (m, 3H), 7.95-7.53 (m, 15H), 7.53-7.28 (m, 3H), 1.68 (s, 6H), 1.58 (s, 6H).

The energy gap of exemplary compound 118 was measured by a method the same as that in Example 1-(3). The absorption edge of the resulting absorption spectrum was determined and found to be 409 nm. Exemplary compound 118 had an energy gap of 3.03 eV.

Furthermore, the ionization potential of exemplary compound 118 was measured by a method the same as that in Example 1-(3). Exemplary compound 118 had an ionization potential of 5.80 eV.

Example 3

Synthesis of Exemplary Compound 310

[Chem. 18]

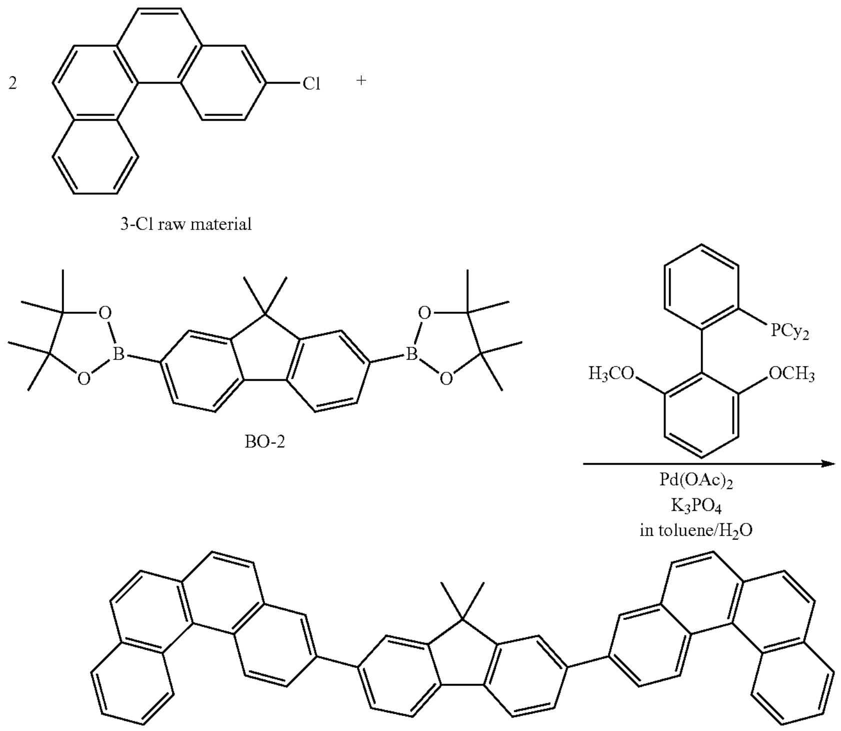

3-Cl raw material

BO-2

Exemplified compound 310

Reagents and solvents described below were charged into a 50-mL recovery flask.

3-Cl raw material: 500 mg (1.90 mmol)
Boronic acid compound BO-2: 425 mg (0.95 mmol)
Palladium(II) acetate: 21 mg (95 μmol)
2-Dicyclohexylphosphino-2',6'-dimethoxybiphenyl: 98 mg (238 μmol)
Potassium phosphate: 1.01 g (4.75 mmol)
Toluene: 25 mL
Water: 0.6 mL The resulting reaction mixture was stirred for 5 hours at 100° C. under nitrogen. After the completion of the reaction, water was added to the reaction mixture. The resulting mixture was stirred to precipitate a product. The precipitated product was filtered to give a gray powder as a crude product. The crude product was dissolved in heated chlorobenzene. The solution was passed through a short silica gel column to remove the residual catalyst. Recrystallization purification was performed twice from a chlorobenzene/octane mixed solvent. The resulting crystals were dried at 150° C. under vacuum and then subjected to sublimation purification at $10^{-4}$ Pa and 385° C. to give 241 mg (yield: 39%) of high-purity exemplary compound 310.

The identification results of the resulting compound were described below.

[MALDI-TOF-MS]

Observed value: m/z=646.39, calculated value: $C_{51}H_{34}$=646.27

[$^1$H-NMR (400 MHz, $CDCl_3$)]

δ 9.25 (d, 2H), 9.20 (d, 2H), 8.33 (d, 2H), 8.15-8.00 (m, 6H), 8.00-7.82 (m, 12H), 7.73 (t, 2H), 7.66 (t, 2H), 1.72 (s, 6H).

The energy gap of exemplary compound 310 was measured by a method the same as that in Example 1-(3). The absorption edge of the resulting absorption spectrum was determined and found to be 416 nm. Exemplary compound 310 had an energy gap of 2.98 eV.

Furthermore, the ionization potential of exemplary compound 310 was measured by a method the same as that in Example 1-(3). Exemplary compound 310 had an ionization potential of 5.82 eV.

Comparative Example 1

Comparison of Energy Gap

The energy gap and ionization potential of each of comparative compounds H01 and H02 illustrated below were measured by methods the same as those in Example 1-(3). Table 2 shows the results together with the results of Examples 1 to 3.

[Chem. 19]

[Comparative compound]

H01

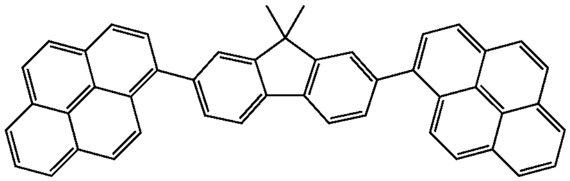

H02

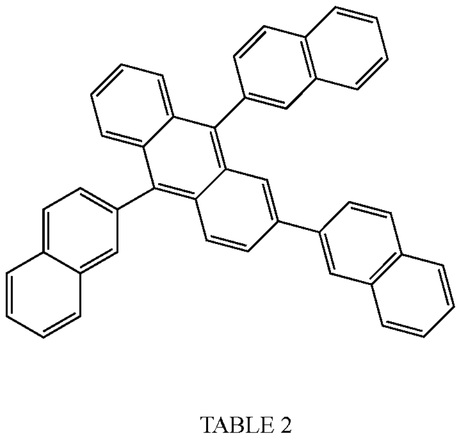

TABLE 2

| | Absorption edge | Energy gap | Ionization potential |
|---|---|---|---|
| Exemplified compound 113 | 407 nm | 3.05 eV | 5.82 eV |
| Exemplified compound 118 | 409 nm | 3.03 eV | 5.80 eV |
| Exemplified compound 310 | 416 nm | 2.98 eV | 5.82 eV |
| Comparative compound H01 | 422 nm | 2.94 eV | 5.77 eV |
| Comparative compound H02 | 429 nm | 2.89 eV | 5.77 eV |

Example 4

In this example, an organic light-emitting device having a structure of anode/hole transport layer/light-emitting layer/electron transport layer/cathode stacked, in that order, on a substrate was produced by a method described below, in which the electron transport layer was formed of two layers having different ionization potentials.

A glass substrate on which an ITO film with 120 nm a thickness of was formed as an anode by sputtering was used as a transparent conductive support substrate (ITO substrate). Organic compound layers and electrode layers described below were continuously formed on the ITO substrate by vacuum evaporation using resistance heating in a vacuum chamber at $10^{-5}$ Pa. In this case, the device was produced so as to have an area of the facing electrodes of 3 $mm^2$.

Hole transport layer (50 nm) HTL-1

Light-emitting layer (30 nm) host: BH-1, guest: BD-1 (weight ratio: 5%)

Electron transport layer 1 (10 nm) exemplary compound 113

Electron transport layer 2 (30 nm) ETL-1

Metal electrode layer 1 (0.5 nm) LiF

Metal electrode layer 2 (100 nm) Al

[Chem. 20]

HTL-1

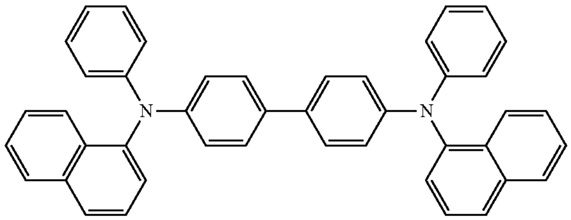

BH-1

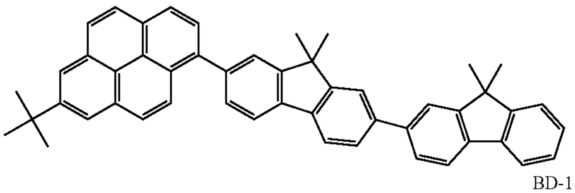

BD-1

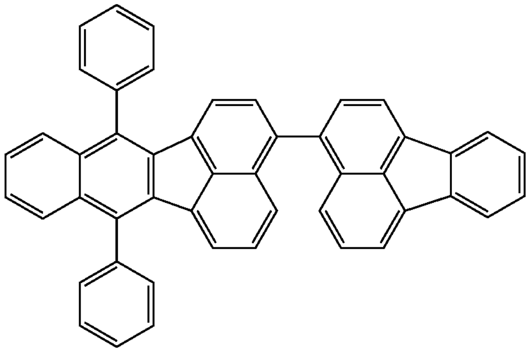

-continued

ETL-1

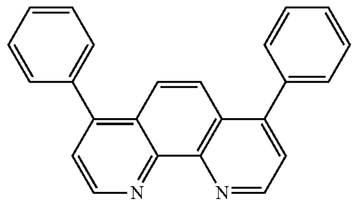

Next, in order to prevent degradation of the organic light-emitting device due to water absorption, the device was covered with a protective glass plate and sealed with an acrylic resin adhesive in a dry air atmosphere. Thereby, the organic light-emitting device was produced.

For the resulting organic light-emitting device, the ITO electrode was used as a positive electrode. The Al electrode was used as a negative electrode. When a voltage of 4.5 V was applied between the electrodes, blue-light emission was observed at a luminous efficiency of 9.3 cd/A and a luminance of 1000 cd/$m^2$. Furthermore, for this device, the CIE chromaticity coordinates was (x, y)=(0.16, 0.25). To check the durability, the device was driven for 100 hours while a constant current density of 100 mA/$cm^2$ was maintained. In this case, the rate of decrease in luminance with respect to the initial luminance was 14%.

Example 5

A device was produced as in Example 4, except that the material of the electron transport layer 1 was changed from exemplary compound 113 to exemplary compound 118. Furthermore, the evaluation of the resulting device was made in the same way as in Example 4. Table 3 shows the results.

Example 6

A device was produced as in Example 4, except that the material of the electron transport layer 1 was changed from exemplary compound 113 to exemplary compound 310. Furthermore, the evaluation of the resulting device was made in the same way as in Example 4. Table 3 shows the results.

Comparative Example 2

A device was produced as in Example 4, except that the material of the electron transport layer 1 was changed from exemplary compound 113 to comparative compound H02. Furthermore, the evaluation of the resulting device was made in the same way as in Example 4. Table 3 shows the results.

In Comparative Example 2, the rate of decrease in luminance is 34%, which exceeds 20%. That is, the degradation of luminance is large. In contrast, the rate of decrease in luminance of each of the organic light-emitting devices was less than 20%. That is, the degradation of luminance is small.

Example 7

In this example, an organic light-emitting device having a structure of anode/hole transport layer/light-emitting layer/electron transport layer/cathode stacked, in that order, on a substrate was produced by a method described below, in which the electron transport layer was formed of two layers having different ionization potentials.

Organic compound layers and electrode layers described below were continuously formed on an ITO substrate, which was produced by a method the same as in Example 4, by vacuum evaporation using resistance heating in a vacuum chamber at $10^{-5}$ Pa. In this case, the device was produced so as to have an area of the facing electrodes of 3 $mm^2$.

Hole transport layer (25 nm) HTL-1
Light-emitting layer (30 nm) host: exemplary compound 113, guest: BD-2 (weight ratio: 5%)
Electron transport layer 1 (10 nm) ETL-2
Electron transport layer 2 (25 nm) ETL-1
Metal electrode layer 1 (0.5 nm) LiF
Metal electrode layer 2 (100 nm) Al

[Chem. 21]

BD-2

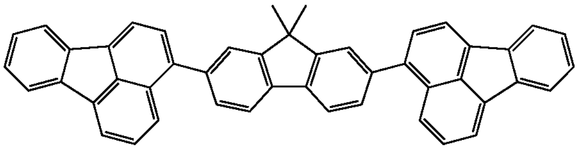

ETL-2

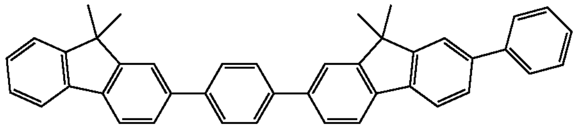

Next, in order to prevent degradation of the organic light-emitting device due to water absorption, the device was covered with a protective glass plate and sealed with an acrylic resin adhesive in a dry air atmosphere. Thereby, the organic light-emitting device was produced.

For the resulting organic light-emitting device, the ITO electrode was used as a positive electrode. The Al electrode was used as a negative electrode. When a voltage of 4.7 V was applied between the electrodes, blue-light emission was observed at a luminous efficiency of 8.0 cd/A and a luminance of 1000 cd/$m^2$. Furthermore, for this device, the CIE chromaticity coordinates was (x, y)=(0.16, 0.26). To check the durability, the device was driven for 100 hours while a constant

TABLE 3

| | Electron transport layer 1 | CIE chromaticity | Applied voltage @1000 cd/$m^2$ (V) | Luminous efficiency @1000 cd/$m^2$ (cd/A) | Rate of decrease in luminance after 200 hours @100 mA/$cm^2$ |
|---|---|---|---|---|---|
| Example 4 | Exemplified compound 113 | (0.16, 0.25) | 4.5 | 9.3 | 14% |
| Example 5 | Exemplified compound 118 | (0.16, 0.23) | 4.7 | 8.9 | 16% |
| Example 6 | Exemplified compound 310 | (0.16, 0.23) | 4.5 | 8.3 | 12% |
| Comparative Example 2 | Comparative compound H02 | (0.15, 0.27) | 4.8 | 5.3 | 34% |

current density of 50 mA/cm$^2$ was maintained. In this case, the rate of decrease in luminance with respect to the initial luminance was 15%.

Example 8

A device was produced as in Example 7, except that the host of the light-emitting layer was changed from exemplary compound 113 to exemplary compound 118. Furthermore, the evaluation of the resulting device was made in the same way as in Example 7. Table 4 shows the results.

Example 9

A device was produced as in Example 7, except that the host of the light-emitting layer was changed from exemplary compound 113 to exemplary compound 310. Furthermore, the evaluation of the resulting device was made in the same way as in Example 7. Table 4 shows the results.

Comparative Example 3

A device was produced as in Example 7, except that the host of the light-emitting layer was changed from comparative compound H01 to exemplary compound 310. Furthermore, the evaluation of the resulting device was made in the same way as in Example 7. Table 4 shows the results.

In Comparative Example 3, the rate of decrease in luminance is 33%, which exceeds 30%. That is, the degradation of luminance is large. In contrast, the rate of decrease in luminance of each of the organic light-emitting devices was less than 30%. That is, the degradation of luminance is small.

-continued

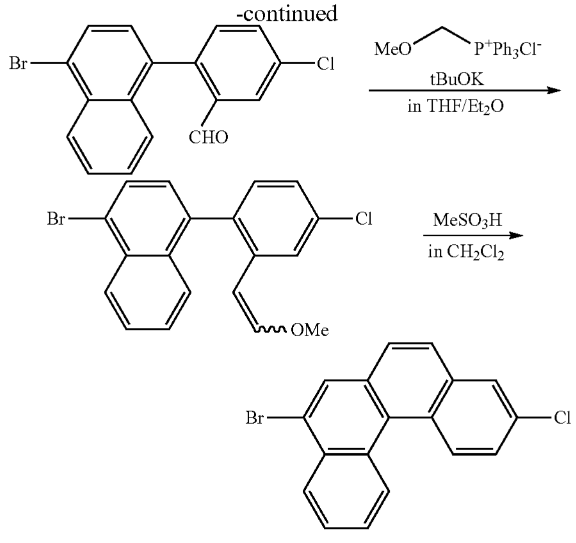

BrCl raw material

Reagents and solvents described below were charged into a 300-mL recovery flask.

1-Bromo-4-iodonaphthalene: 5.00 g (15.0 mmol)

4-Chloro-2-formylphenylboronic acid: 2.64 g (14.3 mmol)

Tetrakis(triphenylphosphine)palladium(0): 0.50 g (0.43 mmol)

TABLE 4

| | Host | CIE chromaticity | Applied voltage @1000 cd/m$^2$ (V) | Luminous efficiency @1000 cd/m$^2$ (cd/A) | Rate of decrease in luminance after 100 hours @50 mA/cm$^2$ |
|---|---|---|---|---|---|
| Example 7 | Exemplified compound 113 | (0.16, 0.26) | 4.7 | 8.0 | 15% |
| Example 8 | Exemplified compound 118 | (0.16, 0.25) | 4.7 | 7.2 | 20% |
| Example 9 | Exemplified compound 310 | (0.16, 0.28) | 4.5 | 8.3 | 24% |
| Comparative Example 3 | Comparative compound H01 | (0.15, 0.29) | 4.2 | 7.0 | 33% |

Example 10

Synthesis of Exemplary Compound 412

(1) Synthesis of BrCl Raw Material

[Chem. 22]

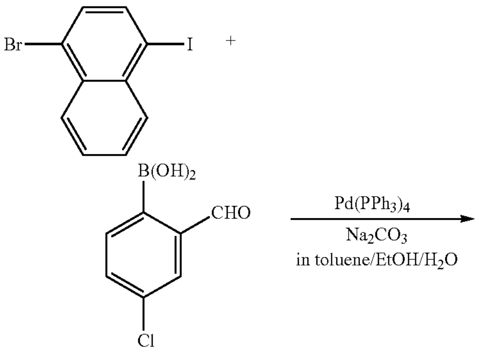

Toluene: 100 mL

Ethanol: 50 mL

Aqueous solution of 10% by weight sodium carbonate: 50 mL

The resulting reaction mixture was heated to reflux for 2.5 hours with stirring under nitrogen. After the completion of the reaction, the reaction solution was washed with water, dried over sodium sulfate, and concentrated to give a crude product. The crude product was then purified by silica gel column chromatography (eluent: heptane/chloroform=3/1) to give 3.90 g (yield: 79%) of oily 1-bromo-4-(4-chloro-2-formylphenyl)naphthalene.

Subsequently, 9.67 g (28.2 mmol) of (methoxymethyl) triphenylphosphonium chloride and 48 mL of dry diethyl ether were charged into a 300-mL recovery flask filled with nitrogen at room temperature. The mixture was stirred. Then 28.2 mL (28.2 mmol) of 1 M tert-butoxypotassium solution in THF was added thereto. The resulting mixture was stirred for 1 hour. Subsequently, a solution of 3.90 g (11.3 mmol) of 1-bromo-4-(4-chloro-2-formylphenyl)naphthalene dissolved in 93 mL of a THF solvent was added to the reaction mixture. After the resulting mixture was stirred for another 4 hours at room temperature, water was added thereto, terminating the reaction. The separation of two phases was performed to recover the aqueous phase. Extraction of the aqueous phase was performed three times with ethyl acetate. The organic phase was washed with water, dried over sodium sulfate, and concentrated to give a crude product. The crude product was then purified by silica gel column chromatography (eluent: heptane/chloroform=20/1) to give 4.17 g (yield: 99%) of 1-bromo-4-(4-chloro-2-methoxyethenylphenyl)naphthalene.

At room temperature, 4.17 g (11.2 mmol) of 1-bromo-4-(4-chloro-2-methoxyethenylphenyl)naphthalene and 63 mL of dry dichloromethane were charged into a 300-mL recovery flask filled with nitrogen. The mixture was stirred. Then 1.2 mL of methanesulfonic acid was added thereto. The resulting mixture was stirred for 4 hours at room temperature. Methanol was added thereto, terminating the reaction. The separation of two phases was performed to recover the organic phase. The organic phase was washed with water, dried over sodium sulfate, and concentrated to give a crude product. The crude product was then purified by silica gel column chromatography (eluent: heptane) to give 334 mg (yield: 9%) of a BrCl raw material (3-chloro-8-bromobenzo[c]phenanthrene).

(2) Synthesis of 8-PhBpin Compound

[Chem. 23]

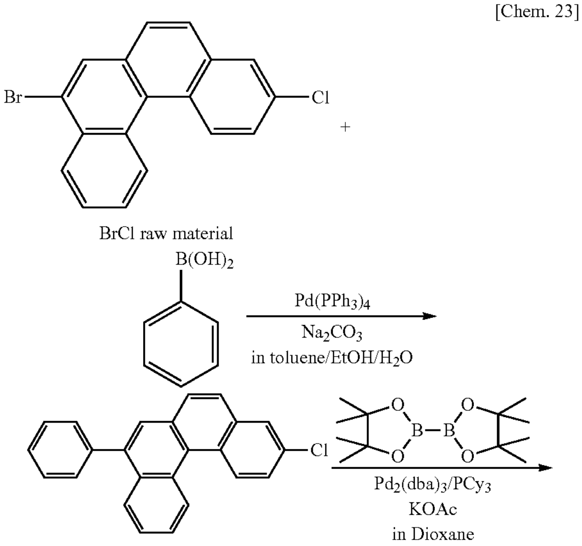

BrCl raw material

8-PhCl compound

-continued

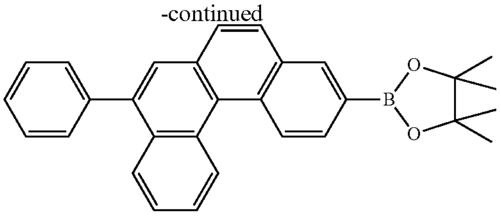

8-PhBpin compound

Reagents and solvents described below were charged into a 50-mL three-necked flask.

BrCl raw material: 260 mg (0.76 mmol)

Phenylboronic acid: 97 mg (0.80 mmol)

Tetrakis(triphenylphosphine)palladium(0): 53 mg (46 μmol)

Toluene: 4 mL

Ethanol: 1 mL

Aqueous solution of 20% by weight sodium carbonate: 2 mL

The resulting reaction mixture was stirred for 4 hours at 90° C. under nitrogen. After cooling, water was added thereto. Extraction was performed with toluene. The organic phase was washed twice with water, dried over magnesium sulfate, and concentrated to give a crude product. The crude product was then purified by silica gel column chromatography (eluent: chloroform/heptane=1/9). Washing was performed with methanol to give 180 mg (yield: 69%) of 8-PhCl compound as a white solid.

Reagents and a solvent described below were charged into a 50-mL recovery flask.

8-PhCl compound: 180 mg (0.53 mmol)

Bis(pinacolato)diboron: 0.20 g (0.79 mmol)

Tris(dibenzylideneacetone)dipalladium(0): 48 mg (53 μmol)

Tricyclohexylphosphine: 37 mg (0.13 mmol)

Potassium acetate: 77 mg (0.79 mmol)

1,4-Dioxane: 5 mL

The resulting reaction mixture was stirred at 95° C. for 3 hours under nitrogen. After cooling, water was added thereto. Extraction was performed with toluene. The organic phase was washed with water, dried over magnesium sulfate, and concentrated to give a crude product. The crude product was then purified by silica gel column chromatography (eluent: chloroform/heptane=1/1). Washing was performed with methanol to give 68 mg (yield: 30%) of a 8-PhBpin compound as a white solid.

(3) Synthesis of Exemplary Compound 412

[Chem. 24]

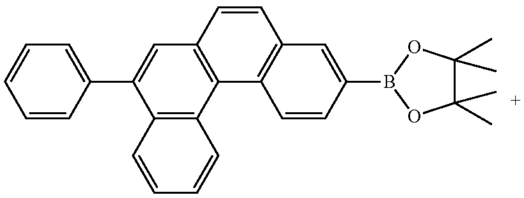

8-PhBpin compound

-continued

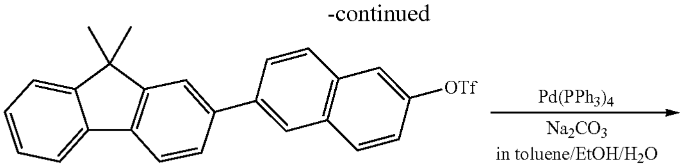

OTf-1

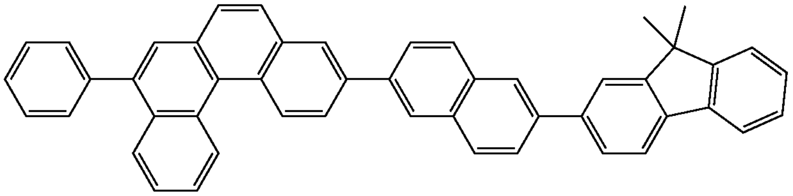

Exemplified compound 412

Reagents and solvents described below were charged into a 50-mL recovery flask.

8-PhBpin compound: 68 mg (0.16 mmol)

OTf-1: 70 mg (0.15 mmol)

Tetrakis(triphenylphosphine)palladium(0): 17 mg (15 μmol)

Toluene: 2 mL

Ethanol: 1 mL

Aqueous solution of 20% by weight sodium carbonate: 1 mL

The resulting reaction mixture was stirred for 2 hours at 90° C. under nitrogen. After cooling, extraction was performed with toluene. The organic phase was washed with water, dried over magnesium sulfate, and concentrated to give a crude product. The crude product was then purified by silica gel column chromatography (eluent: chloroform/heptane=1/4). Washing was performed with methanol to give 68 mg (yield: 69%) of exemplary compound 412 as a white solid.

The identification results of the resulting compound were described below.

[$^1$H-NMR (500 MHz, $CDCl_3$)]

δ 9.26 (t, 2H, J=9.5 Hz), 8.41 (s, 1H), 8.33 (s, 1H), 8.19 (s, 1H), 8.14 (d, 1H, J=8.5 Hz), 8.04-8.11 (m, 5H), 7.90 (d, 2H, J=8.5 Hz), 7.86 (d, 1H, J=8.0 Hz), 7.83 (s, 2H), 7.72-7.80 (m, 3H), 7.64 (d, 2H, J=8.0 Hz), 7.55-7.61 (m, 3H), 7.47-7.51 (m, 2H), 7.34-7.40 (m, 2H), 1.60 (s, 6H).

The energy gap of exemplary compound 412 was measured by a method the same as that in Example 1-(3). The absorption edge of the resulting absorption spectrum was determined and found to be 409 nm. Exemplary compound 412 had an energy gap of 3.03 eV.

Furthermore, the ionization potential of exemplary compound 412 was measured by a method the same as that in Example 1-(3). Exemplary compound 412 had an ionization potential of 5.63 eV.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-274965, filed Dec. 2, 2009, which is hereby incorporated by reference herein in its entirety.

The invention claimed is:

1. A benzo[c]phenanthrene compound represented by formula [3]:

[Chem. 6]

[3]

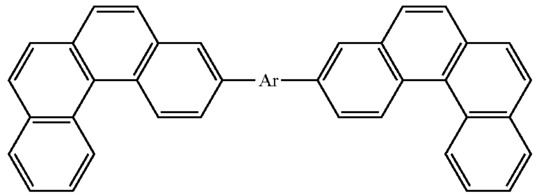

wherein Ar represents a naphthalenediyl group or a fluorenediyl group;

and the Ar may have an alkyl group as a substituent.

2. A benzo[c]phenanthrene compound represented by formula [3]:

[3]

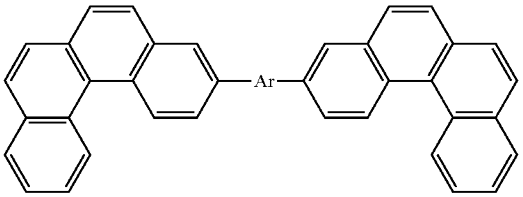

wherein Ar represents an aromatic hydrocarbon group or a heteroaromatic group;

the aromatic hydrocarbon group is selected from the group consisting of a phenyl group, a naphthyl group, a fluorenyl group, a phenanthrenyl group, an anthracenyl group, a fluoranthenyl group, a chrysenyl group, a pyrenyl group, a tetracenyl group, a naphthacenyl group, a triphenylenyl group, a benzofluoranthenyl group, and a perylenyl group;

the heteroaromatic group is selected from the group consisting of a pyridyl group, a pyrazinyl group, a pyrimidinyl group, a pyridazinyl group, a quinolyl group, an isoquinolyl group, an azafluorenyl group, a diazafluorenyl group, a naphthyridinyl group, a quinoxalinyl group, a carbazolyl group, a phenanthridinyl group, a phenanthrolinyl group, an acridinyl group, a phenazinyl group, a thienyl group, a benzothienyl group, a dibenzothienyl group, a furyl group, a benzofuryl group, an isobenzofuryl group, a dibenzofuryl group, an oxazolyl group, an oxadiazolyl group, a thiazolyl group, and a thiadiazolyl group;

and the Ar may have an alkyl group as a substituent.

3. A benzo[c]phenanthrene compound according to claim 2, represented by formula [3]:

[3]

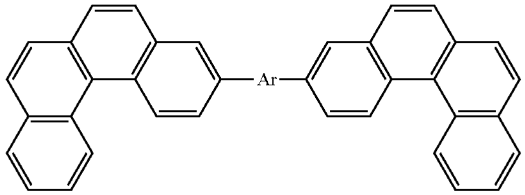

wherein Ar represents an aromatic hydrocarbon group or a heteroaromatic group;

the aromatic hydrocarbon group is selected from the group consisting of a phenyl group, a naphthyl group, and a fluorenyl group;

the heteroaromatic group is selected from the group consisting of a pyridyl group, a diazafluorenyl group, a naphthyridinyl group, a phenanthrolinyl group, an oxadiazolyl group, and a thiadiazolyl group;

and the Ar may have an alkyl group as a substituent.

4. An organic light-emitting device comprising:

a pair of electrodes; and an organic compound layer provided between the pair of electrodes, wherein the organic compound layer contains the benzo[c] phenanthrene compound according to claim 2.

5. The organic light-emitting device according to claim 4, wherein the organic compound layer serves as an electron transport layer, and the electron transport layer is arranged between a light-emitting layer and a cathode.

6. The organic light-emitting device according to claim 4, wherein the organic compound layer serves as a light-emitting layer.

7. A display comprising:

a plurality of pixels, wherein each of the pixels includes the organic light-emitting device according to claim 4, and a switching element, and wherein one electrode of the pair of electrodes included in the organic light-emitting device is connected to a drain electrode or a source electrode of the switching element.

8. An image input device comprising:

a display unit; and an image input unit configured to read an image, wherein the display unit includes a plurality of pixels, wherein each of the pixels includes the organic light-emitting device according to claim 4, and a switching element, and wherein one electrode of the pair of electrodes included in the organic light-emitting device is connected to one of a drain electrode and a source electrode of the switching element.

9. A lighting apparatus comprising the organic light-emitting device according to claim 4.

10. An image forming apparatus comprising an exposure light source, the exposure light source comprising the organic light-emitting device according to claim 4.

11. An exposure light source of an image forming apparatus comprising the organic light-emitting device according to claim 4.

12. A device comprising a substrate and the organic light-emitting device according to claim 4.

13. The device according to claim 12, further comprising a color filter.

* * * * *